US010517853B2

(12) United States Patent
Welch et al.

(10) Patent No.: US 10,517,853 B2
(45) Date of Patent: Dec. 31, 2019

(54) METHODS FOR TREATING EPILEPSY

(71) Applicant: PTC Therapeutics, Inc., South Plainfield, NJ (US)

(72) Inventors: Ellen Welch, Califon, NJ (US); Yuki Tomizawa, Jersey City, NJ (US); Priya Vazirani, South Amboy, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 15/771,379

(22) PCT Filed: Oct. 28, 2016

(86) PCT No.: PCT/US2016/059262
§ 371 (c)(1),
(2) Date: Apr. 26, 2018

(87) PCT Pub. No.: WO2017/075312
PCT Pub. Date: May 4, 2017

(65) Prior Publication Data
US 2018/0333397 A1  Nov. 22, 2018

Related U.S. Application Data

(60) Provisional application No. 62/248,891, filed on Oct. 30, 2015.

(51) Int. Cl.
*A61K 31/4245* (2006.01)
*A61K 31/535* (2006.01)
*A61P 25/08* (2006.01)

(52) U.S. Cl.
CPC ........ *A61K 31/4245* (2013.01); *A61K 31/535* (2013.01); *A61P 25/08* (2018.01)

(58) Field of Classification Search
CPC .... A61K 31/4245; A61K 31/535; A61P 25/08
See application file for complete search history.

(56) References Cited

U.S. PATENT DOCUMENTS

| 3,192,103 | A  | 6/1965  | Sousa et al. |
| 4,016,170 | A  | 4/1977  | Nadelson |
| 4,022,901 | A  | 5/1977  | Venkatachala et al. |
| 4,135,910 | A  | 9/1979  | Howe |
| 4,166,732 | A  | 9/1979  | Howe |
| 4,210,762 | A  | 7/1980  | Howe |
| 4,268,299 | A  | 5/1981  | Howe |
| 5,484,944 | A  | 1/1996  | Albaugh et al. |
| 5,972,050 | A  | 10/1999 | Wiesenfeldt et al. |
| 6,034,106 | A  | 3/2000  | Biftu et al. |
| 6,071,700 | A  | 6/2000  | Feng |
| 6,180,648 | B1 | 1/2001  | Kozikowski et al. |
| 6,472,422 | B2 | 10/2002 | Kozikowski et al. |
| 6,498,151 | B2 | 12/2002 | Li et al. |
| 6,620,828 | B2 | 9/2003  | Chu et al. |
| 6,660,753 | B2 | 12/2003 | Van Wagenen et al. |
| 6,759,538 | B2 | 7/2004  | Singh et al. |
| 6,992,096 | B2 | 1/2006  | Karp et al. |
| 7,041,685 | B2 | 5/2006  | Cai et al. |
| 7,112,595 | B2 | 9/2006  | Van Wagenen et al. |
| 7,153,880 | B2 | 12/2006 | Singh et al. |
| 7,202,262 | B2 | 4/2007  | Karp et al. |
| 7,304,080 | B2 | 12/2007 | Karp et al. |
| 7,419,991 | B2 | 9/2008  | Karp et al. |
| 7,435,750 | B2 | 10/2008 | Cai et al. |
| 7,678,922 | B2 | 3/2010  | Almstead et al. |
| 7,683,082 | B2 | 3/2010  | Karp et al. |
| 7,745,630 | B2 | 6/2010  | Bryans et al. |
| 7,772,259 | B2 | 8/2010  | Karp et al. |
| 7,863,456 | B2 | 1/2011  | Almstead et al. |
| 8,017,636 | B2 | 9/2011  | Karp et al. |
| 8,101,641 | B2 | 1/2012  | Almstead et al. |
| 8,129,540 | B2 | 3/2012  | Karp et al. |
| 8,163,782 | B2 | 4/2012  | Karp et al. |
| 8,227,494 | B2 | 7/2012  | Karp et al. |
| 8,299,105 | B2 | 10/2012 | Karp et al. |
| 8,367,841 | B2 | 2/2013  | Almstead et al. |
| 8,394,966 | B2 | 3/2013  | Almstead et al. |
| 8,486,982 | B2 | 7/2013  | Karp et al. |
| 8,691,511 | B2 | 4/2014  | Almstead et al. |
| 8,716,321 | B2 | 5/2014  | Hirawat et al. |
| 8,748,625 | B2 | 6/2014  | Almstead et al. |

(Continued)

FOREIGN PATENT DOCUMENTS

| CA | 2342432 A1 | 3/2001 |
| EP | 675122 A2 | 10/1995 |

(Continued)

OTHER PUBLICATIONS

Miller et. al., Human Molecular Genetics, 2013, Oxford University Press, vol. 22(13), pp. 2723-2734 (Year: 2013).*
Liang et. al., Epilepsia, 2011, Wiley Periodicals Inc., vol. 52(10), pp. 1835-1842 (Year: 2011).*
Chiron et. al., Epilepsia, 2011, Wiley Periodicals Inc., vol. 52(suppl. 2), pp. 72-75 (Year: 2011).*
Castren et. al., European Journal of Paediatric Neurology, 2011, Elsevier, vol. 15, pp. 65-69 (Year: 2011).*
U.S. Appl. No. 60/149,464, filed Aug. 19, 1999, Van Wagenen et al.
U.S. Appl. No. 60/269,847, filed Feb. 21, 2001, Van Wagenen et al.
U.S. Appl. No. 60/350,107, filed Nov. 2, 2001, Singh et al.
U.S. Appl. No. 60/405,472, filed Aug. 23, 2002, Singh et al.
Announcement by PTC Therapeutics, Inc. and Genzyme Corporation dated Mar. 3, 2010.

(Continued)

*Primary Examiner* — Sarah Pihonak
(74) *Attorney, Agent, or Firm* — Jones Day

(57) ABSTRACT

Provided herein are methods of treating, preventing, ameliorating or managing a nonsense mutation mediated epileptic disease, comprising administering a 1,2,4-oxadiazole benzoic acid to a patient having a nonsense mutation mediated epileptic disease. In particular, provided herein are methods of treating, preventing, ameliorating or managing a CDKL5 and/or SCN1A (Dravet syndrome) nonsense mutation mediated epileptic disease.

8 Claims, 6 Drawing Sheets

Specification includes a Sequence Listing.

(56) References Cited

U.S. PATENT DOCUMENTS

| | | |
|---|---|---|
| 8,796,322 B2 | 8/2014 | Karp et al. |
| 8,815,838 B2 | 8/2014 | Griffith et al. |
| 8,975,287 B2 | 3/2015 | Karp et al. |
| 9,205,088 B2 | 12/2015 | Karp et al. |
| 9,226,919 B2 | 1/2016 | Hirawat et al. |
| 9,289,398 B2 | 3/2016 | Almstead et al. |
| 9,309,206 B2 | 4/2016 | Almstead et al. |
| 9,474,743 B2 | 10/2016 | Hirawat et al. |
| 9,522,137 B2 | 12/2016 | Hirawat et al. |
| 9,737,513 B2 | 8/2017 | Hirawat et al. |
| 9,873,677 B2 | 1/2018 | Weetall et al. |
| 9,877,952 B2 | 1/2018 | Hirawat et al. |
| 10,071,081 B2 | 4/2018 | Karp et al. |
| 10,028,939 B2 | 7/2018 | Almstead et al. |
| 10,034,863 B2 | 7/2018 | Hirawat et al. |
| 10,172,836 B2 | 1/2019 | Hirawat et al. |
| 2002/0147188 A1 | 10/2002 | Marquis et al. |
| 2004/0229257 A1* | 11/2004 | Petrou .............. C07K 14/705 435/6.16 |
| 2010/0088778 A1 | 4/2010 | Mulley et al. |
| 2010/0168109 A1 | 7/2010 | Karp et al. |
| 2012/0022109 A1* | 1/2012 | Quattropani ........ C07D 271/06 514/326 |
| 2012/0289476 A1 | 11/2012 | Barth et al. |
| 2014/0343009 A1 | 11/2014 | Barth et al. |
| 2016/0081988 A1 | 3/2016 | Karp et al. |
| 2016/0101087 A1 | 4/2016 | Hirawat et al. |
| 2017/0196842 A1 | 7/2017 | Weetall et al. |
| 2018/0179170 A1 | 6/2018 | Weetall et al. |
| 2018/0296538 A1 | 10/2018 | Almstead et al. |
| 2018/0311219 A1 | 11/2018 | Hirawat et al. |
| 2019/0099405 A1 | 4/2019 | Hirawat et al. |

FOREIGN PATENT DOCUMENTS

| | | |
|---|---|---|
| JP | 2001-247569 | 9/2001 |
| JP | 2002-105073 | 4/2002 |
| JP | 2003-081832 | 5/2004 |
| RU | 2398770 C1 | 9/2010 |
| WO | WO 95/11885 | 5/1995 |
| WO | WO 97/09335 | 3/1997 |
| WO | WO 97/41105 | 11/1997 |
| WO | WO 97/44333 | 11/1997 |
| WO | WO 97/46556 | 12/1997 |
| WO | WO 98/00465 | 1/1998 |
| WO | WO 98/33927 | 8/1998 |
| WO | WO 98/45263 | 10/1998 |
| WO | WO 98/49190 | 11/1998 |
| WO | WO 99/21852 | 5/1999 |
| WO | WO 99/54317 | 10/1999 |
| WO | WO 2000/021951 A1 | 4/2000 |
| WO | WO 2000/021959 | 4/2000 |
| WO | WO 2000/025768 | 5/2000 |
| WO | WO 2000/038687 | 7/2000 |
| WO | WO 2000/058278 | 10/2000 |
| WO | WO 2000/058280 | 10/2000 |
| WO | WO 2000/058304 | 10/2000 |
| WO | WO 2000/069810 | 11/2000 |
| WO | WO 2000/075120 | 12/2000 |
| WO | WO 2001/066534 | 9/2001 |
| WO | WO 2001/083464 | 11/2001 |
| WO | WO 2001/085723 | 11/2001 |
| WO | WO 2001/090101 | 11/2001 |
| WO | WO 2002/072621 | 9/2002 |
| WO | WO 2002/079200 | 10/2002 |
| WO | WO 2002/085869 | 10/2002 |
| WO | WO 2002/100826 | 12/2002 |
| WO | WO 2003/002559 | 1/2003 |
| WO | WO 2004/014370 | 2/2004 |
| WO | WO 2004/014902 | 2/2004 |
| WO | WO 2004/072050 | 8/2004 |
| WO | WO 2004/085401 | 10/2004 |
| WO | WO 2004/091502 | 10/2004 |
| WO | WO 2004/110351 | 12/2004 |
| WO | WO 2005/060961 | 7/2005 |
| WO | WO 2005/077373 | 8/2005 |
| WO | WO 2006/044682 A1 | 4/2006 |
| WO | WO 2006/110483 A1 | 10/2006 |
| WO | WO 2007/117438 A2 | 10/2007 |
| WO | WO 2007/123848 A2 | 11/2007 |
| WO | WO 2008/030570 A1 | 3/2008 |
| WO | WO 2008/039431 A2 | 4/2008 |
| WO | WO 2008/045566 A1 | 4/2008 |
| WO | WO 2008/127364 A2 | 10/2008 |
| WO | WO 2008/130370 | 10/2008 |
| WO | WO 2009/023509 A2 | 2/2009 |
| WO | WO 2009/043889 A2 | 4/2009 |
| WO | WO 2009/054725 A2 | 4/2009 |
| WO | WO 2009/079562 A2 | 6/2009 |
| WO | WO 2010/008831 A2 | 1/2010 |
| WO | WO 2011/072281 | 6/2011 |
| WO | WO 2012/016930 | 2/2012 |
| WO | WO 2015/134711 | 9/2015 |
| WO | WO 2015/188037 | 12/2015 |

OTHER PUBLICATIONS

Au et al., 1998, "Germ-Line Mutational Analysis of the TSC2 Gene in 90 Tuberouse-Sclerosis Patients," Am. J. Hum. Genet. 62:286-294.

Auld et al., 2009, "Mechanism of PTC124 activity in cell-based luciferase assays of nonsense codon suppression", Proc Natl Acad Sci USA; 106(9):3585-3590.

Auld et al., 2010, "Molecular basis for the high-affinity binding and stabilization of firefly luciferase by PTC124", Proc Natl Acad Sci USA; 107(11):4878-4883.

Aurino et al., 2006, "Readthrough strategies for stop codons in Duchenne muscular dystrophy", Acta Myologica; 25(1):5-12.

Davies et al., 2008, "Ataluren nonsense mutation suppressor treatment of cystic fibrosis treatment of muscular dystrophy", Drugs of the Future; 33(9):733-736.

Du et al., 2008, "PTC124 is an orally bioavailable compound that promotes suppression of the human CFTR-G542X nonsense allele in a CF mouse model", Proc Natl Acad Sci USA; 105(6):2064-2069.

Gite et al., 2003, "A high-throughput nonisotopic protein truncation test" Nature Biotechnology 21:194-197.

Guillonneau et al., 1999, "A nonsense mutation in a novel gene is associated with retinities pigmentosa in a family linked to the RP1 locus" Human Molecular Genetics 8:1541-1546.

Hamed et al., 2006, "Drug evaluation: PTC-124—a potential treatment for cystic fibrosis and Duchenne muscular dystrophy", IDrugs; 9(11):783-789.

Hirawat et al., 2007, "Safety, Tolerability, and Pharmacokinetics of PTC124, a Nonaminoglycoside Nonsense Mutation Suppressor, Following Single- and Multiple-Dose Administration to Healthy Male and Femal Adult Volunteers,"Journal of Clinical Pharmacology 47(4):430-444.

Hu et al., 2008, "New approaches to treatment of primary immunodeficiencies: fixing mutations with chemicals"; Curr Opin Allergy Clin Immunol; 8(6):540-546.

Jones et al., 1999, "Comprehensive Mutation Analysis of TSC1 and TSC2—and Phenotypic Correlations in 150 Families with Tuberous Sclerosis," Am. J. Hum. Genet. 64:1305-1315.

Jones et al., 2009, "Emerging treatments in cystic fibrosis", Drugs; 69(14):1903-1910.

Kerem et al., 2008, "Effectiveness of PTC124 treatment of cystic fibrosis caused by nonsense mutations: a prospective phase II trial", Lancet; 372(9640):719-727.

Koeberl et al.,1990, "Recurrent nonsense mutations at arginine residues cause severe hemophilia B in unrelated hemophiles" Hum. Genet. 84:387-390.

Laake et al., 2000, "Characterization of ATM Mutations in 41 Nordic Families With Ataxia Telangiectasia"Human Mutation 16:232-246.

Litjens et al., 2001, "Mucopolysaccharidosis Type VI: Structural and Clinical Implications of Mutations in N-Acetylgalactosamine-4-Sulfatase" Human Mutation 18:282-295.

(56) References Cited

OTHER PUBLICATIONS

MacDonald et al., 2003, "Design and synthesis of trans-3-(2-(4-((3-(5-methyl1-1,2,4-oxadiazolyl))-phenyl)carboxamido)cycolhexyl)ethyl)-7-methylsulfonyl-2,3,4,5-tetrahydro-1H-3-benzazepine (SB-414796):a potent and selective dopamine D3 receptor antagonist", J Med Chem; 46(23):4952-4964.
Matsuda et al., 2008, "Recent development of read through therapy for muscular dystrophy", Igaku no Ayumi; 226(5):397-401.
Mueller, G., *Chem. Ber.*, 19:1497 (1886).
Ogami et al., 2010, "Research on mRNA degradation and drug discovery", Nihon Yakurigaku Zasshi; 136(3):150-154 (with English Abstract).
Rowe et al., 2009, "Pharmaceuticals targeting nonsense mutations in genetic diseases: progress in development", BioDrugs; 23(3):165-174.
Sands et al., 1993, "A single-base-pair deletion in the β-glucuronidase gene accounts for the phenotype of murine mucopolysaccharidosis type VIII" *Proc. Natl. Acad. Sci. USA* 90:6567-6571.
Schrijver et al., 2002, "Premature Termination Mutations in FBN1: Distinct Effects on Differential Allelic Expression and on Protein and Clinical Phenotypes" *Am. J. Hum. Genet.* 71:223-237.
Sokolenko et al., 1972, Voprosy Khimii I Khimicheskoi Tekhnologii No. 27:107-112 (with English language abstract).
Strizheva et al., 2001, "The Spectrum of Mutations in TSC1 and TSC2 in Women with Tuberous Sclerosis and Lymphangiomyomatosis," *Am. J. Respir. Crit. Care Med.* 163:253-258.
Supplemental Information from Auld et al., 2009, "Mechanism of PTC124 activity in cell based luciferase assays of nonsense codon suppression," Proc Natl Acad Sci USA; 106(9):3585-3590, pp. 1-17.
Supplementary Information from Welch et al., 2007, "PTC124 Targets Genetic Disorders Caused by Nonsense Mutations," *Nature* 447:87-91 (pp. 1-23).
Sweeney, 2009, "Suppression of premature atop codons for the treatment of a subset of patients with genetic disorders", J Med Sci; 2(1):1-4.
Wakamatsu et al., 1999, "Mutations producing premature termination of translation and an amino acid substitution in the sterol 27-hydroxylase gene cause cerebrotendinous xanthomatosis associated with parkinsonism" *J. Neurol. Neurosurg. Psychiaatry* 67:195-198.
Wang et al., 2010, "Membrane blebbing as an assessment of functional rescue of dysferlin-deficient human myotubes via nonsense suppression", *J Appl Physiol*; 109(3):901-905.
Welch et al., 2007, "PTC124 Targets Genetic Disorders Caused by Nonsense Mutations," *Nature* 447:87-91.
Wolf et al., 2008, "Don't stop me now! A new active substance with the abbreviation PTC124 targets genetic disorders caused by nonsense mutations", Pharmazie in Unaerer Zeit; 37(5):356-357.
Yogalingam et al., 2001, "Molecular Genetics of Mucopolysaccharidosis Type IIIA and IIIB: Diagnostic, Clinical, and Biological Implications" *Human Mutation* 18:264-281.
Stahl et al. Handbook of Pharmaceutical Salts, Wiley & Sons, 2008, p. 215.
International Search Report dated Jan. 24, 2017 in connection with International Patent Application No. PCT/US16/59262, filed Oct. 28, 2016.
Written Opinion of the International Searching Authority dated Jan. 24, 2017 in connection with International Patent Application No. PCT/US16/59262, filed Oct. 28, 2016.
Huang et al., 2012, "The GABRG2 Nonsense Mutation, Q40X, Associated with Dravet Syndrom Activated NMD and Generated a Truncated Subunit That was Partially Rescued by aminoglycoside-Induced Stop Codon Read-through" *Neurobiol. Dis.* 48(1): 115-123.
Scriver et al., The Metabolic & Molecular Bases of Inherited Disease 8$^{th}$ Ed., vol. IV, Chapter 230, Noebels, "The Inherited Epilepsies," McGraw-Hill, 2008, pp. 5807-5832.
Nectoux et al., 2006, "Maternal origin of a novel C-terminal truncation mutation in CDKL5 causing a severe atypical form of Rett syndrome" *Clin. Genet.* 70: 29-33.
Mulley et al., 2005, "SCN1A Mutations and Epilepsy" *Human Mutation* 25: 535-542.
Walker et al., 2015, "Personalized medicine approaches in epilepsy" *Journal of Internal Medicine* 277: 218-234.
Carranza Rojo et al., 2011, "De novo SCN1A mutations in migrating partial seizures of infancy" Neurology 77: 380-383.
Claes et al., 2001, "De Novo Mutations in the Sodium-Channel Gene SCN1A Cause Severe Myoclonic Epilepsy of Infancy" *Am. J. Hum. Genet.* 68: 1327-1332.
Catterall et al., 2010, "NaV1.1 channels and epilepsy" *J. Physiol.* 588: 1849-59.
Dravet, 2011, "Dravet syndrome history" Dev. Med. Child Neurol. 53 (Supple. 2): 1-6.
Devinsky, 2011, Sudden, unexpected death in epilepsy N. Engl. J. Med. 365(19): 1801-11.
Fehr et al., 2013, "The CDKL5 disorder is an independent clinical entity associated with early-onset encephalopathy" Eur. J. Human Genet. 21(30: 266-73.
Genton et al., 2011, "Dravet syndrome: the long-term outcome" Epilepsia 52(Suppl. 2):44-9.
Mei et al., 2010, "Xp22.3 genomic deletions involving the CDKL5 gene in girls with early onset epileptic encephalopathy" Epilepsia 51(4): 647-54.
Melani et al., 2011, "CDKL5 gene-related epileptic encephalopathy: electroclinical findings in the first year of life" Dev. Med. Child Neurol. 53(4): 354-60.
Rusconi et al., 2008, "CDKL5 expression is modulated during neuronal development and its subcellular is distrubtiontightly regulated by the C-terminal tail" J. Biol. Chem. 283(44): 30101-11.
Sabaz et al., 2003, "Validation of the quality life in childhood epilepsy questionaire in American epilepsy patients" Epilepsy Behav. 4(6):680-91.
Pack AM., Sudep, What Are the Risk Factors? Do Seizures or Antiepileptic Drugs Contribute to an Increased Risk?, Epilepsy Currents, vol. 12, No. 4 Jul./ Aug. 2012 pp. 131-132.
Mari et al., 2005, "CDKL5 Belongs to the Same Molecular Pathway of MeCP2 and it is Responsible for the Early-Onset Seizure Variant of Rett Syndrome" Human Molecular Genetics 14(14): 1935-1946.
Yu et al., 2006, "Reduced Sodium Current in GABAergic Interneurons in a Mouse Model of Severe Myoclonic Epilepsy in Infancy" Nature Neuroscience 9(9): 1142-1149.
Dravet et al., 2005, "Severe Myoclonic Epilepsy in Infancy: Dravet Syndrome" in: Epileptic Syndromes in Infancy, Childhood and Adolescence, 4th edition John Libbey Eurotext 2005 Chapter 7 p. 89-113).
Chieffo et al., 2011, "Neuropsychological Development in Children with Dravet Syndrome, Epilepsy Research" 95: 86-93.
Frame Katheryn, Elibri DO. The International CDKL5 Disorder Database, Newsletter 1 (Jul. 2013).
Ceulemans et al., 2004, "Clinical Correlations of Mutations in the SCN1A Gene: From Febrile Seizures to Severe Myoclonic Epilepsy in Infancy." Pediatric Neurology 30(4):236-243.
Kang and MacDonald 2009, "Making sense of nonsense $GABA_A$ receptor mutations associated with genetic epilepsies." Trends in Molecular Medicine 15(9):430-438.
Keeling et al., 2014, "Therapeutics Based on Stop Codon Readthrough." Annual Reviews of Genomics and Human Genetics. 15:371-394. Available in PMC Feb. 13, 2017.
Kilstrup-Nielsen et al., 2012, "What We Know and Would Like to Know about CDKL5 and Its Involvement in Epileptic Encephalopathy." Neural Plasticity. vol. 2012, Article ID: 728267. doi:10.1155/2012/728267. 11 pages.
Miller et al., 2014, "The novel $Cln1^{R151X}$ mouse model of infantile neuronal ceroid lipofuscinosis (INCL) for testing nonsense suppression therapy." Human Molecular Genetics 24(1):185-196. Advance Access published Sep. 8, 2014.
Welch et al., 2007, "PTC124 targets genetic disorders caused by nonsense mutations." Nature 447(7140):87-91. Published online Apr. 22, 2007.

(56) References Cited

OTHER PUBLICATIONS

Extended European Search Report dated May 27, 2019 for EP Application No. 16860855.2.

* cited by examiner

SEQUENCE LISTING

```
<160> NUMBER OF SEQ ID NOS: 3

<210> SEQ ID NO 1
<211> LENGTH: 49
<212> TYPE: DNA
<213> ORGANISM: Artificial Sequence
<220> FEATURE:
<223> OTHER INFORMATION: SCN1A sequence with TAG nonsense mutation
      (Trp192X nonsense codon)

<400> SEQUENCE: 1
```

```
aagattttac tttccttcgg gatccatgga actagctcga tttcactgt            49

<210> SEQ ID NO 2
<211> LENGTH: 82
<212> TYPE: DNA
<213> ORGANISM: Artificial Sequence
<220> FEATURE:
<223> OTHER INFORMATION: CDKL5 sequence with TAG nonsense mutation
      (T59X nonsense codon)

<400> SEQUENCE: 2
cgtacgaaga aaatgaagaa gtcaaagaaa cgactttatg agagcttaaa atgcttcgga   60
ctctcaagca ggaaaacgta cg                                            82

<210> SEQ ID NO 3
<211> LENGTH: 88
<212> TYPE: DNA
<213> ORGANISM: Artificial Sequence
<220> FEATURE:
<223> OTHER INFORMATION: CDKL5 sequence with TAG nonsense mutation
      (R550X nonsense codon)

<400> SEQUENCE: 3
cgtacgacac gagaactttg ctcagcccctt ctggaagaaa taactgaaat gagggaacgc  60
tggactcacg tcgaaccaca accgtacg                                      88
```

METHODS FOR TREATING EPILEPSY

This application is a national stage entry of International Patent Application No. PCT/US2016/059262, filed Oct. 28, 2016, which claims the benefit of U.S. Provisional Application No. 62/248,891, filed Oct. 30, 2015, each of which is incorporated herein by reference in its entirety.

1. FIELD

Provided herein are methods of treating, preventing, ameliorating or managing a nonsense mutation mediated epileptic disease, comprising administering a 1,2,4-oxadiazole benzoic acid compound (e.g., 3-[5-(2-fluoro-phenyl)-[1,2,4] oxadiazol-3-yl]-benzoic acid) to a patient having a nonsense mutation mediated epileptic disease, e.g., a patient having a nonsense mutation in the CDKL5 or SCN1A gene. In particular, provided herein are methods of treating, preventing, ameliorating or managing a nonsense mutation mediated epileptic disease associated with a genetic or somatic nonsense mutation in the CDKL5 or SCN1A gene, wherein the nonsense mutation results in expression of a premature stop codon, comprising administering a 1,2,4-oxadiazole benzoic acid compound (e.g., 3-[5-(2-fluoro-phenyl)-[1,2,4] oxadiazol-3-yl]-benzoic acid) to a patient having the nonsense mutation.

2. BACKGROUND

Drug-resistant epilepsy is a serious condition that negatively impacts patients' quality of life. Those with drug-resistant epilepsy are at a higher risk for sudden unexpected death in epilepsy (SUDEP). The risk factors associated with SUDEP, including frequent generalized tonic-clonic seizures, antiepileptic drug (AED) polytherapy, and common nocturnal seizures, are also factors present in those with drug-resistant epilepsy (Pack A M., SUDEP, What Are the Risk Factors? Do Seizures or Antiepileptic Drugs Contribute to an Increased Risk?, Epilepsy Currents, Vol. 12, No. 4 (July/August) 2012 pp. 131-132). The risk of SUDEP in those with drug-resistant epilepsy can exceed 5% per decade (Devinsky O. N Engl J Med. 2011; 365(19):1801-11). Most patients with drug-resistant epilepsy, despite trials of multiple combinations of AEDs, have no Food and Drug Administration (FDA)-approved treatment options left. CDKL5 and SCN1A related epilepsies are rare epilepsies commonly associated with drug-resistant epilepsy.

CDKL5 is a gene that produces the cyclin-dependent kinase-like 5 (CDKL5) protein that is primarily expressed in the brain, thymus, and testes. The gene is composed of 24 exons; exons 2-11 code for the catalytic domain whereas exons 12-18 code for the carboxy-terminus. In mice, the expression profile suggests that the CDKL5 protein is involved in neuronal maturation (Rusconi et al., J Biol Chem., 2008; 283(44):30101-11). CDKL5 phosphorylates the protein product of the MECP2 gene in the nucleus and likely accounts for the similarity between Rett syndrome and CDKL5 related epilepsies (Mari F., Azimonti S., Bertani I., Bolognese F., Colombo E., Caselli R., Scala E., Longo I., Grosso S., Pescucci C., Ariani F., Hayek G., Balestri P., Bergo A., Badaracco G., Zappella M., Broccoli V., Renieri A., Kilstrup-Nielsen C., Landsberger N., CDKL5 Belongs to the Same Molecular Pathway of MeCP2 and it is Responsible for the Early-Onset Seizure Variant of Rett Syndrome, Human Molecular Genetics, 2005, Vol. 14, No. 14, 1935-1946). MECP2 regulates genes associated with synapse function and maintenance. Loss of this function drives phenotype and is responsible for similarities to Rett syndrome. CDKL5 also phosphorylates DNA methyltransferase 1 (DNMT1) and amphiphysin, and interacts with Rac1 to influence actin remodeling and neuronal morphogenesis.

CDKL5 related epilepsies are X-linked genetic epileptic encephalopathies most often present in females. Males are more severely affected than females (Melani et al., Dev Med Child Neurol. 2011; 53(4):354-60). The incidence is ~1 in 45,000 live births. Patients with CDKL5 related X-linked genetic epileptic encephalopathies exhibit early signs of poor developmental skills, (e.g., poor sucking, poor eye contact) in the first several months of life. Later, impairment of hand motor skills, lack of speech acquisition, and severe and global developmental delays become apparent (Fehr et al., Eur J Hum Genet. 2013; 21(3):266-73; Melani et al., Dev Med Child Neurol. 2011; 53(4):354-60). Eye contact and social interactions are often reduced. Many patients are never able to walk independently. CDKL5 related epilepsies are not associated with cortical atrophy or degeneration. CDKL5 deficiency causes an epileptic encephalopathy, in which epileptiform abnormalities contribute to progressive functional impairment. Epilepsy often presents with infantile spasms within the first four months of age (Mei et al., Epilepsia. 2010 April; 51(4):647-54). The average age of seizure onset is 6 weeks with more than 90% experiencing seizures in the first 3 months of life. Later, tonic-clonic seizures consisting of a vibratory tonic phase followed by a clonic phase occur and often last 2 to 4 minutes (Melani et al., Dev Med Child Neurol. 2011; 53(4):354-60). After age 3 years, seizures remit in many children while others continue to have drug-resistant epilepsy, with tonic spasms and of myoclonic seizures (Mei et al., Epilepsia. 2010 April; 51(4):647-54). The electroencephalogram findings often include slowing of the background with interictal generalized, focal or multifocal discharges. A burst-suppression pattern may be seen in younger children (Melani et al., Dev Med Child Neurol. 2011; 53(4):354-60).

SCN1A (Nav1.1) is the sodium channel α1 subunit gene, expressed almost exclusively in the brain. Mutations in SCN1A can cause a variety of epilepsies that range from benign febrile seizures to severe epileptic encephalopathy and Dravet syndrome (severe myoclonic epilepsy of infancy; Mulley et al., Hum Mutat. 2005; 25(6):535-42; Catterall et al., J Physiol. 20101; 588(Pt 11):1849-59). The major mechanism underlying epilepsy appears to be impairment of gamma-Aminobutyric acid (GABA) interneuron inhibitory function (Catterall et al., J Physiol. 20101; 588(Pt 11):1849-59; Yu F H., Mantegazza M., Westenbroek R E., Robbins C A., Kalume F., Burton K A., Spain W J., McKnight G S., Scheuer T., Catterall W A., Reduced Sodium Current in GABAergic Interneurons in a Mouse Model of Severe Myoclonic Epilepsy in Infancy, Nature Neuroscience, 2006, September, Vol. 9, No. 9, 1142-1149).

Dravet syndrome was initially described in 1978 as Severe Myoclonic Epilepsy of Infancy (SMEI) by Charlotte Dravet (Dravet C. Dev Med Child Neurol. 2011; 53(Suppl 2):1-6). It causes febrile and afebrile, generalized and unilateral, clonic or tonic-clonic seizures; it can also cause absence, absence-myoclonic, and complex partial seizures. Seizures typically begin in the first year of life in an otherwise normal infant. Initial seizures are often febrile status epilepticus (Dravet C., Bureau M., Oguni H., Fukuyama Y., Cokar O., Severe Myoclonic Epilepsy in Infancy: Dravet Syndrome, Adv. Neurol. (2005), 95, 71-102). Later, myoclonic, atypical absence, and partial seizures often develop. Seizures are usually drug-resistant but the severity of the epilepsy tends to diminish around puberty. Developmental delays in the second year of life and intellectual disability are present in more than 95% of patients (Chieffo D., Battaglia D., Lettori D., Del Re M., Brogna C., Dravet C., Mercuri E., Guzzetta F., Chieffo, D., Chieffo, D., Neuropsychological Development in Children with Dravet Syndrome, Epilepsy Research, (2011), 95, 86-93). Autism spectrum disorder is diagnosed in approximately 25% of patients (Genton et al., Epilepsia. 2011; 52(Suppl 2):44-9). Most patients develop cerebellar dysfunction in later childhood, manifesting as an ataxic gait disorder, dysarthria, and intention tremor (Genton et al., Epilepsia. 2011; 52(Suppl 2):44-9). The mortality rate is high. Approximately 15% of patients die by adolescence and 20% die by early adulthood (Genton et al., Epilepsia. 2011; 52(Suppl 2):44-9). SUDEP and status epilepticus are the most common causes of death.

Nonsense mutations are single-point alterations in the DNA that, when transcribed, result in conversion of a messenger ribonucleic acid (mRNA) triplet (e.g., CAG) that codes for an amino acid to a triplet (e.g., UAG) that is interpreted as a stop codon (i.e., a premature stop codon). The presence of the premature stop codon within the mRNA leads to production of a truncated, non-functional protein and consequent disease. Nonsense mutations are the basis for approximately 13% to 40% of the individual cases of most inherited disease, including CDKL5 deficiency and SCN1A deficiency (in particular, Dravet syndrome) amongst many others (Frame Katheryn, Elibri DO. The International CDKL5 Disorder Database Newsletter 1 (July 2013)).

3. SUMMARY OF THE DISCLOSURE

Provided herein are methods of treating, preventing, ameliorating or managing a nonsense mutation mediated epileptic disease and/or an epileptic disease associated with a premature stop codon, comprising administering a 1,2,4-oxadiazole benzoic acid (e.g., 3-[5-(2-fluoro-phenyl)-[1,2,4]oxadiazol-3-yl]-benzoic acid) to a patient having a nonsense mutation mediated epileptic disease. In particular, provided herein are methods of treating, preventing, ameliorating or managing an epileptic disease associated with a nonsense mutation or a premature stop codon (e.g., resulting in a CDKL5 and/or SCN1A deficiency (in particular, Dravet syndrome); or, e.g., a SCN2A, GABRG2, DEPDC5, and/or NAPB deficiency), comprising administering a 1,2,4-oxadiazole benzoic acid (e.g., 3-[5-(2-fluoro-phenyl)-[1,2,4]oxadiazol-3-yl]-benzoic acid) to a patient having an epileptic disease associated with a nonsense mutation or a premature stop codon (e.g., resulting in a CDKL5 and/or SCN1A deficiency (in particular, Dravet syndrome); or, e.g., a SCN2A, GABRG2, DEPDC5, and/or NAPB deficiency).

4. BRIEF DESCRIPTION OF THE DRAWINGS

5. DETAILED DESCRIPTION

5.1. Definitions

Figure 1:
FIG. 1 is a schematic showing the reporter construct used to monitor readthrough activity of SCN1A nonsense codon W192X. The SCN1A nucleotide sequence used in the reporter construct is shown (SEQ ID NO: 1) with the TAG nonsense mutation (W192X) indicated by gray shading.

As used herein, the term "premature translation termination" has the same meaning as commonly understood by one of ordinary skill in the art. In certain embodiments, the term "premature translation termination" generally refers to the result of a mutation that changes a codon corresponding to an amino acid to a stop codon. In specific embodiments, the term "premature translation termination" refers to the event during translation where production of a functional protein ceases as the result of a nonsense mutation in DNA that changes a transcribed mRNA codon corresponding to an amino acid to a premature stop codon.

As used herein, the terms "premature termination codon" and "premature stop codon" have the same meaning as commonly understood by one of ordinary skill in the art. In certain embodiments, the terms "premature termination codon" and "premature stop codon" refer to the occurrence of a stop codon where a codon corresponding to an amino acid should be.

As used herein, the term "nonsense mutation" has the same meaning as commonly understood by one of ordinary skill in the art. In certain embodiments, the term "nonsense mutation" refers to a mutation in DNA that changes a codon in mRNA corresponding to an amino acid to a stop codon. In certain embodiments, the nonsense mutation is a mutation that occurs in DNA and is then transcribed as a premature stop codon into mRNA.

As used herein, the term "nonsense suppression" has the same meaning as commonly understood by one of ordinary skill in the art. In certain embodiments, the term "nonsense suppression" refers to the inhibition or suppression of premature translation termination, resulting in production of a functional protein.

As used herein, the term "modulation of premature translation termination" refers to an increase in the amount of functional protein produced by readthrough of a premature stop codon in the presence of a nonsense suppression agent. In certain embodiments, to treat, prevent, ameliorate or manage a nonsense mutation mediated disease, it is desirable to increase the production of a protein encoded by a mRNA with a premature stop codon, i.e., to enable readthrough of the premature stop codon resulting from expression of the disease gene so translation of the mRNA can occur through the use of a nonsense suppression agent.

As used herein, the terms "active agent," "drug," and "drug substance" refer to a 1,2,4-oxadiazole benzoic acid compound selected from 3-[5-(2-fluoro-phenyl)-[1,2,4]oxadiazol-3-yl]-benzoic acid (having the generic name "ataluren") or a pharmaceutically acceptable salt thereof provided herein and collectively referred to herein as "Compound 1".

As used herein, the term "dose(s)" means a quantity of active agent to be administered at one time.

As used herein, the term "unit dosage form(s)" includes solid dosage forms such as tablets, caplets, capsules, lozenges, dispersions, powders, granules or gels and the like or liquid dosage forms such as solutions, suspensions, emulsions or elixirs and the like and solid forms such as powders or granules that can be reconstituted to provide such liquid dosage forms, wherein such unit dosage form(s) are suitable for oral or parenteral administration to a patient.

As used herein, the terms "dosing regimen" and "dosage(s)" mean the amount of an active agent administered over a given time period, per patient weight.

As used herein, the terms "subject" and "patient" are used interchangeably to refer to an animal or any living organism having sensation and the power of voluntary movement, and which requires for its existence oxygen and organic food. Non-limiting examples include members of the human, primate, equine, porcine, bovine, leporine, *rattus*, murine, canine and feline species. In some embodiments, the subject is a mammal or a warm-blooded vertebrate animal. In certain embodiments, the subject is a non-human animal. In specific embodiments, the subject is a human and, further, a human patient. In certain embodiments, the subject is a fetus, embryo, infant, child, adolescent or adult. In one embodiment, the subject has been determined through genetic pre-screening to possess a nonsense mutation. In another embodiment, the subject has been determined through genetic pre-screening to have a particular premature stop codon (i.e., UAA, UGA, or UAG). In another embodiment, the context of the premature stop codon in the subject has been determined from the genetic pre-screening (i.e., UAAA, UAAC, UAAU, UAAG, UGAA, UGAC, UGAU, UGAG, UAGA, UAGC, UAGU or UAGG).

As used herein, the term "effective amount" in the context of the production of a functional read-through protein refers to the amount of the functional read-through protein(s) that has a prophylactic and/or therapeutic benefit to a subject. In specific embodiments, an effective amount of a functional read-through protein is the amount of protein that has in one, two or more of the following effects: (1) prevents the onset, development and/or progression of a nonsense mutation mediated epileptic disease, (2) prevents the onset, development and/or progression of one or more symptoms associated with a nonsense mutation mediated epileptic disease, (3) reduces the duration and/or severity of a nonsense mutation mediated epileptic disease, (4) reduces the number of symptoms associated with a nonsense mutation mediated epileptic disease, (5) reduces the duration of one or more symptoms associated with a nonsense mutation mediated epileptic disease, (6) reduces the severity of one or more symptoms associated with a nonsense mutation mediated epileptic disease and (7) improves the quality of life of a subject.

Symptoms of a nonsense mutation mediated epileptic disease include convulsive seizures, drop seizures, generalized unilateral (one-sided) clonic seizures or generalized tonic clonic (grand mal) seizures, characterized by unconsciousness, convulsions, and muscle rigidity; absence seizures, characterized by a short loss of consciousness; generalized myoclonic seizures, characterized by sporadic jerks, usually on both sides of the body; generalized clonic seizures, characterized by repetitive, rhythmic jerks that involve both sides of the body at the same time; generalized tonic seizures, characterized by stiffening of the muscles; generalized atonic seizures, characterized by a sudden and general loss of muscle tone, particularly in the arms and legs, which often results in a fall; simple motor partial seizures, characterized by awareness, jerking, muscle rigidity, spasms, head-turning; simple sensory partial seizures, characterized by awareness and unusual sensations affecting either the vision, hearing, smell taste, or touch; simple psychological partial seizures, characterized by awareness and memory or emotional disturbances; complex partial seizures (focal dyscognitive seizures), characterized by impairment of awareness and automatisms such as lip smacking, chewing, fidgeting, walking and other repetitive, involuntary but coordinated movements; partial seizures with secondary generalization, characterized by preservation of consciousness that then evolves into a loss of consciousness and convulsions; sudden unexpected death in epilepsy (SUDEP); and nocturnal seizures.

As used herein, the term "effective amount" in the context of the administration of a compound described herein refers to the amount of the compound that has a prophylactic and/or therapeutic benefit to a subject. In specific embodiments, an effective amount of a compound described herein that has one, two or more of the following effects: (1) prevents the onset, development and/or progression of a nonsense mutation mediated epileptic disease, (2) prevents the onset, development and/or progression of one or more symptoms associated with a nonsense mutation mediated epileptic disease, (3) reduces the duration and/or severity of a nonsense mutation mediated epileptic disease, (4) reduces the number of symptoms associated with a nonsense mutation mediated epileptic disease, (5) reduces the duration of one or more symptoms associated with a nonsense mutation mediated epileptic disease, (6) reduces the severity of one or more symptoms associated with a nonsense mutation mediated epileptic disease and/or (7) improves the quality of life of a subject. Examples of effective amounts of a compound described herein are provided in Section 5.4, infra. In specific embodiments, an effective amount of a compound described herein has one, two or more of the foregoing effects when used for treating, preventing, ameliorating or managing a symptom or nonsense mutation mediated epileptic disease provided herein in Section 6, infra.

As used herein, the term "functional" in the context of a functional read-through protein refers to a protein that is produced in a sufficient quantity to treat, prevent or ameliorate a disease that results from the absence of the protein. In addition, the term refers to a protein that has enough of the functional activity of the wild-type protein to have a beneficial effect in a cell or subject which otherwise does not produce or produces insufficient amounts of the wild-type protein as a result of a mutation (e.g., a nonsense mutation) in the nucleic acid sequence (e.g., gene) encoding the protein. In a specific embodiment, the functional read-through protein(s) substantially performs the function of the full-length wild-type protein(s), i.e., treating, preventing, ameliorating or managing the disease. In another specific embodiment, the functional read-through protein(s) performs one, two, three or more of the functions of the full-length wild-type protein(s). In certain embodiments, the functional read-through protein(s) produced is a functional non-wild-type protein(s). In certain embodiments, the functional read-through protein(s) produced is the functional wild-type protein(s). In some embodiments, the functional non-wild-type protein produced is full-length. In some embodiments, the functional wild-type protein produced is full-length. In other embodiments, the functional non-wildtype protein(s) is not full-length. In other embodiments, the functional wild-type protein(s) produced is not full-length.

As used herein, the term "substantially performs the function of the full-length wild-type protein(s)," in the context of a functional read-through protein(s), means that the functional read-through protein(s) performs at least one, two, three, or more functions of the full-length wild-type protein(s).

As used herein, the term "nonsense mutation mediated epileptic disease" refers to an epileptic disease or condition or a type of epilepsy resulting either directly or indirectly from a nonsense mutation(s) in a gene(s), where the nonsense mutation(s) prevents production of a wild-type protein in an affected cell. For example, a nonsense mutation in the CDKL5 gene prevents the production of a wild-type CDKL5 protein and results in a CDKL5 nonsense mutation mediated epileptic disease. Also, for example, a nonsense mutation in the SCN1A gene prevents the production of a wild-type SCN1A protein and results in SCN1A nonsense mutation mediated epileptic disease (in particular, Dravet syndrome). Examples of nonsense mutation mediated epileptic diseases include, but are not limited to Dravet syndrome, Severe myoclonic epilepsy of infancy (SMEI), CDKL5, SCN1A, Generalized epilepsy with febrile seizures plus (GEFS+), Temporal lobe epilepsy, Intractable childhood epilepsy, Benign familial neonatal-infantile seizures (BFNIS), Benign familial neonatal seizures (BFNIS), Juvenile myoclonic epilepsy (JME), Childhood absence epilepsy (CAE), Autosomal dominant nocturnal frontal lobe epilepsy (ADNFLE), Cryptogenic generalized epilepsy (CGE), Cryptogenic focal epilepsy (CFE), Myoclonic astatic epilepsy (MAE), Severe idiopathic generalized epilepsy of infancy (SIGEI), Infantile spasms (IS), and Early-onset epileptic encephalopathy (EOEE).

As used herein, "in combination" in the context of the administration of therapies refers to the use of more than one therapy. The use of the term "in combination" does not restrict the order in which therapies are administered to a subject with a disease. In certain embodiments, administration of one or more therapies to a subject with a disease includes, without limitation, a first therapy that can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to a disease. The therapies are administered to a subject in a sequence and within a time interval such that a unit dosage form(s) described herein can act together with another therapy to provide an increased benefit than if the therapies were administered alone.

As used herein, the terms "manage," "managing" and "management" refer to the beneficial effects that a patient derives from the administration of a pharmaceutical composition provided herein comprising 3-[5-(2-fluoro-phenyl)-[1,2,4]oxadiazol-3-yl]benzoic acid or a salt thereof, which does not result in treating, preventing or ameliorating the nonsense mutation mediated disease.

As used herein, the terms "prevent," "preventing" and "prevention" refer to the prevention (e.g., avoidance) of the onset, recurrence, spread or worsening of the nonsense mutation mediated disease or a symptom thereof (and thus treat or, at least, ameliorate such disease) in a patient from the administration of a pharmaceutical composition provided herein comprising administering Compound 1 or a salt thereof to a patient with such a disease. Since diseases associated with a nonsense mutation have a genetic or somatic basis, requiring a patient to be screened for the presence of a nonsense mutation. When it is determined through screening that a patient has a nonsense mutation, an effective amount of a pharmaceutical composition comprising an effective amount of 3-[5-(2-fluoro-phenyl)-[1,2,4] oxadiazol-3-yl]benzoic acid or a salt thereof provided herein can be administered to the patient to prevent the onset, recurrence, spread or worsening of the disease or a symptom thereof.

As used herein, the terms "treat," "treating" and "treatment" refer to the eradication or amelioration of the disease or symptoms associated with the disease. In certain embodiments, such terms refer to minimizing the spread or worsening of the disease in a patient from the administration of a pharmaceutical composition provided herein comprising 3-[5-(2-fluoro-phenyl)-[1,2,4]oxadiazol-3-yl]benzoic acid or a salt thereof provided herein to a patient with such a disease. When it is determined that a patient has a disease associated with a genetic or somatic nonsense mutation, an effective amount of a pharmaceutical composition comprising an effective amount of 3-[5-(2-fluoro-phenyl)-[1,2,4] oxadiazol-3-yl]benzoic acid or a salt thereof provided herein can be administered to the patient to eradicate, ameliorate, or minimize the spread or the worsening of the disease or a symptom thereof.

As used herein, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, the term "wild-type" in the context of a protein refers to a protein that is found in nature (often, but not necessarily, the protein that is the predominant protein whose absence is responsible for the disease) and is designated as a standard or reference protein.

5.2. The Compound

A compound for use in the preparation of the pharmaceutical compositions and salts provided herein is 3-[5-(2-fluoro-phenyl)-[1,2,4]oxadiazol-3-yl]-benzoic acid (generically referred to as ataluren), having the structure of Formula (I):

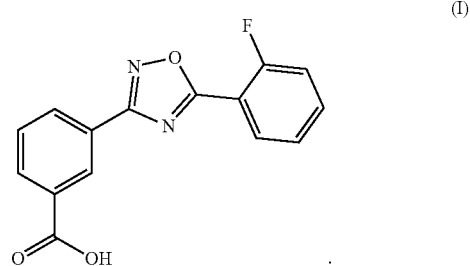 [SMILES: O=C(O)c1cccc(-c2noc(-c3ccccc3F)n2)c1]

A compound of Formula (I) can be prepared according to the methods described in U.S. Pat. Nos. 6,992,096, 7,678, 922 and 8,367,841, the disclosure of each of which is incorporated by reference herein in its entirety. Alternatively, a compound of Formula (I) can be also prepared according to other methods apparent to those of skill in the art based upon the teaching herein. All such alternative methods are intended to be included within the scope of the methods described herein. The compound of Formula (I) and salts provided herein are collectively referred to as "Compound 1."

In one embodiment, the compound of Formula (I) used in the pharmaceutical compositions, processes, and methods provided herein is a free acid. In one embodiment, the free acid is a solid. In yet another embodiment, the solid free acid is a crystalline form described in U.S. Pat. No. 7,863,456, the disclosure of which is incorporated by reference herein in its entirety. In yet another embodiment, the solid free acid is a crystalline Form A. In yet another embodiment, the solid free acid is a crystalline Form B. These solid forms of the compound of Formula (I) can also be prepared according to the methods described in U.S. Pat. No. 7,863,456, the disclosure of which is incorporated by reference herein in its entirety. Alternatively, the solid forms of the compound of Formula (I) can be also prepared according to other methods apparent to those of skill in the art based upon the teaching herein.

In another embodiment, the free acid of the compound of Formula (I) is a pharmaceutically acceptable solvate. In one embodiment, the free acid is a hydrate. In another embodiment, the compound of Formula (I) is a pharmaceutically acceptable anhydrous form.

In another embodiment, Compound 1 used in the pharmaceutical compositions, processes, and methods provided herein is a pharmaceutically acceptable free acid of the compound of Formula (I). In another embodiment, Compound 1 used in the pharmaceutical compositions, processes, and methods provided herein is a pharmaceutically acceptable salt of the compound of Formula (I). In another embodiment, Compound 1 used in the pharmaceutical compositions, processes, and methods provided herein is a pharmaceutically acceptable anhydrous free acid or salt of the compound of Formula (I).

5.3. Salt Forms

In certain embodiments, the methods provided herein comprise the use of salt forms of Formula (I), including salts selected from L-arginine, L-histidine, L-lysine, N-methyl glucamine, magnesium methoxide, potassium hydroxide, sodium hydroxide or tromethamine (PCT Application No. PCT/US2015/018889, filed Mar. 5, 2015, published as International Patent Application No. WO 2015/134711, which is incorporated by reference herein in its entirety). More particularly, the methods provided herein comprise the use of salt forms of Formula (I) selected from L-lysine, sodium and tromethamine.

5.4. Pharmaceutical Compositions

Pharmaceutical compositions and single unit dosage forms comprising an effective amount of Compound 1 can be used in the methods provided herein. Individual dosage forms may be suitable for oral, dermal, mucosal (including, without limitation, sublingual, buccal, rectal, nasal, or vaginal) or parenteral (including, without limitation, subcutaneous, intramuscular, intraarterial, intraperitoneal, intrathecal, intraventricular, intraurethral, intrasternal, intracranial, intrasynovial, intravesical or intravenous) or ocular administration. Preferred pharmaceutical compositions and single unit dosage forms are suitable for oral administration.

In certain embodiments, the pharmaceutical composition comprises from about 0.1% to about 99%, from about 5% to about 90%, from about 5% to about 50%, from about 10% to about 40%, from about 20% to about 30%, from about 0.1% to about 5%, from about 0.1% to about 2.5%, from about 0.1% to about 1% or from about 0.25% to about 0.5% by weight of Compound 1. In certain embodiments, the pharmaceutical composition comprises about 0.1%, about 0.25%, about 0.5%, about 1%, about 2%, about 5%, about 10%, about 15%, about 20%, about 25%, about 30%, about 35%, about 40%, about 50%, about 60%, about 70%, about 80%, or about 90% by weight of Compound 1. In certain embodiments, the pharmaceutical composition comprises about 0.25%, about 0.5% or about 1% by weight of Compound 1.

In certain embodiments, the pharmaceutical composition provided herein comprises from about 1 mg to about 5,000 mg, from about 10 mg to about 2,000 mg, from about 50 mg to about 1,000 mg, from about 100 mg to about 1,000 mg, or from about 100 mg to about 500 mg of Compound 1. In certain embodiments, the pharmaceutical composition provided herein comprises about 125 mg, about 200 mg, about 325 mg, about 400 mg, or about 500 mg of Compound 1. In certain embodiments, the pharmaceutical composition provided herein comprises from about 120 mg to about 130, from about 195 mg to about 205 mg, from about 320 mg to about 330 mg, from about 395 mg to about 405 mg, or from about 495 mg to about 505 mg of Compound 1.

In certain embodiments, Compound 1 in the pharmaceutical compositions provided herein is the free acid of 3-[5-(2-fluoro-phenyl)-[1,2,4]oxadiazol-3-yl]-benzoic acid or a salt of 3-[5-(2-fluoro-phenyl)-[1,2,4]oxadiazol-3-yl]-benzoic acid, as provided herein.

The pharmaceutical compositions provided herein can be provided in a unit dosage form or multiple-dosage form. A unit dosage form, as used herein, refers to a physically discrete unit suitable for administration to a human or animal subject using packaging known in the art. Each unit-dose contains a predetermined quantity of an active ingredient(s) sufficient to produce the desired therapeutic effect, in association with the required pharmaceutical carriers or excipients. Examples of a unit dosage form include, without limitation, an individually packaged packet, sachet or bottle or dropper. A unit dosage form may be administered in fractions or multiples thereof. A multiple-dosage form is a plurality of identical unit dosage forms packaged in a single container to be administered as segregated or combined unit dosage forms. Examples of a multiple-dosage form include a packet or sachet of granules or powder, a vial or bottle of tablets or capsules, or a bottle of liquid solution in fluid ounces, pints or gallons for administration either parenterally, orally or ocularly via dropper.

The pharmaceutical compositions provided herein can be administered as a divided dose over a period of time. It is understood that the precise dosage and duration of treatment may vary with the age, weight, and condition of the patient being treated, and may be determined empirically using known testing protocols or by extrapolation from in vivo or in vitro test or diagnostic data or by observation of certain clinical factors. It is further understood that for any particular individual, specific dosage regimens may be adjusted over time according to the individual need and the professional judgment of the person administering or supervising the administration of the pharmaceutical composition.

5.4.1. Topical Formulations

In certain embodiments, the pharmaceutical compositions provided herein are formulated as topical formulations in cosolvents such as, but not limited to, dimethyl sulfoxide, propylene glycol and the like.

5.4.2. Oral Formulations

In certain embodiments, the pharmaceutical compositions provided herein are formulated for oral administration. In certain embodiments, the pharmaceutical compositions provided herein for oral administration are provided in solid, semisolid, or liquid dosage forms for oral administration. As used herein, oral administration also includes buccal, lingual, and sublingual administration. Suitable oral dosage forms include, but are not limited to, tablets, sublingual or buccal films (i.e., "fast-melts"), chewable tablets, effervescent tablets, dispersible tablets, mini-tablets, capsules, pills, strips, troches, lozenges, pastilles, oral film, cachets, pellets, medicated chewing gum, bulk powders or granules, effervescent or non-effervescent powders or granules, oral mists, solutions, emulsions, suspensions, wafers, sprinkles, elixirs, and syrups. In addition to the active ingredient, the pharmaceutical compositions can contain one or more pharmaceutically acceptable carriers or excipients including, but not limited to, binders, fillers, diluents, disintegrants, wetting agents, surfactants, lubricants, glidants, pH-modifiers, coloring agents, dye-migration inhibitors, sweetening agents, flavoring agents, emulsifying agents, suspending and dispersing agents, preservatives, solvents, solvating agents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose (CMC), carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEC®-PH-101, AVICEC®-PH-103, AVICEL® RC-581, AVICEl® -PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methyl cellulose and carboxymethyl cellulose; wood products; natural sponge; cation-exchange resins; alginic acid; gums, such as guar gum and VEEGUM® HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric, fumaric acid, ascorbic acid and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein as a tablet for oral administration can be provided as compressed tablets, tablet triturates, chewable lozenges, rapidly dissolving tablets, effervescent tablets, mini tablets, beads, coated beads, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredient from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, solvating agent or emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, ethylenediamine tetraacetic acid (EDTA), hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems.

The pharmaceutical compositions provided herein for oral administration can be provided as either non-effervescent or effervescent tablets or granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

In certain embodiments, the pharmaceutical composition is formulated as a solid oral dosage form. In certain embodiments, the pharmaceutical composition is formulated as a liquid oral dosage form. In certain embodiments, the unit dosage form is provided as a suspension after being mixed in a pharmaceutically acceptable liquid or semi-solid solvating agent, which includes, but is not limited to, water, milk, carbonated beverage, juice, fruit juice, fruit punch, applesauce, yogurt, pudding, ice cream, baby food, baby formula or a soy or grain based product.

In certain embodiments, provided herein are pharmaceutical compositions, which comprise 3-[5-(2-fluoro-phenyl)-[1,2,4]oxadiazol-3-yl]benzoic acid or a pharmaceutically acceptable salt thereof and one or more additional pharmaceutically acceptable excipients. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules. In another embodiment, the one or more excipients are selected from the group consisting of polydextrose, mannitol, poloxamer, polyethylene glycol, hydroxyethyl cellulose, crospovidone, artificial flavoring, and magnesium stearate. In certain embodiments, the artificial flavoring is an artificial vanilla flavor.

Additionally provided herein are pharmaceutical composition comprising about 25% by weight of 3-[5-(2-fluoro-phenyl)-[1,2,4]oxadiazol-3-yl]-benzoic acid or a pharmaceutically acceptable salt thereof; about 1% by weight of colloidal silicon dioxide; and one or more additional pharmaceutically acceptable excipients. In certain embodiments, pharmaceutical compositions provided herein comprise 3-[5-(2-fluoro-phenyl)-[1,2,4]oxadiazol-3-yl]-benzoic acid or a pharmaceutically acceptable salt thereof and one or more excipients selected from polydextrose, poloxamer (e.g., poloxamer 407), polyethylene glycol (e.g., polyethylene glycol 3350), mannitol, hydroxyethyl cellulose, artificial vanilla flavoring, crospovidone, colloidal silicon dioxide, and magnesium stearate (e.g., of vegetable origin). In certain embodiments, pharmaceutical compositions provided herein comprise 3-[5-(2-fluoro-phenyl)-[1,2,4]oxadiazol-3-yl]-benzoic acid or a pharmaceutically acceptable salt thereof and one or more excipients selected from a suspending agent, a binding agent that can also provide taste-masking, surfactant agent, a disintegrant and other excipients can be present. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules. In another embodiment, 3-[5-(2-fluoro-phenyl)-[1,2,4]oxadiazol-3-yl]-benzoic acid or a pharmaceutically acceptable salt thereof is present in an amount such as at about 25% by weight). In another embodiment, the one or more excipients are selected from the group consisting of polydextrose, mannitol, poloxamer, polyethylene glycol, hydroxyethyl cellulose, crospovidone, artificial vanilla flavor, and magnesium stearate. In another embodiment, the one or more excipients (and their proportions of the total formulation weight) are selected from the group consisting of a suspending agent such as Litesse® Ultra [refined polydextrose] at about 26% by weight, a binding agent such as mannitol at about 26% by weight, surfactant agents such as polyethylene glycol 3350 at about 10.0% by weight and Lutrol® micro F127 [poloxamer 407 powder] at about 4% by weight, a disintegrant such as crospovidone at about 5% by weight, and other excipients, each less than about 2% by weight such as cab-o-sil, hydroxyethyl cellulose, magnesium stearate [non-bovine] at about 1% by weight and colloidal silicon dioxide at about 1% by weight.

Further provided herein are pharmaceutical compositions comprising about 25% by weight of 3-[5-(2-fluoro-phenyl)-[1,2,4]oxadiazol-3-yl]-benzoic acid or a pharmaceutically acceptable salt thereof, about 26% by weight of polydextrose, about 26% by weight of mannitol, about 3% by weight of poloxamer, about 10% by weight of polyethylene glycol, about 2% by weight of hydroxyethyl cellulose, about 5% by weight of crospovidone, about 1% by weight of artificial vanilla flavor, about 1% by weight of colloidal silicon dioxide and about 1% by weight of magnesium stearate. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules.

Further provided herein are pharmaceutical compositions comprising, [3-[5-(2-fluoro-phenyl)-[1,2,4]oxadiazol-3-yl]-benzoic acid or a pharmaceutically acceptable salt thereof in a range of from about 120 mg to about 1005 mg, polydextrose in a range of from about 133 mg to about 1030 mg, mannitol in a range of from about 137 mg to about 901 mg, poloxamer in a range of from about 19 mg to about 147 mg, polyethylene glycol in a range of from about 52 mg to about 402 mg, hydroxyethyl cellulose in a range of from about 7 mg to about 59 mg, crospovidone in a range of from about 26 mg to about 201 mg, artificial vanilla flavor in a range of from about 3 mg to about 29 mg, colloidal silicon dioxide in a range of from about 5 mg to about 39 mg and magnesium stearate in a range of about 5 mg to about 39 mg. In one embodiment, the pharmaceutical composition is formulated as powder. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules.

Further provided herein are pharmaceutical compositions, comprising about 130 mg of 3-[5-(2-fluoro-phenyl)-[1,2,4]oxadiazol-3-yl]-benzoic acid or a pharmaceutically acceptable salt thereof, about 133 mg of polydextrose, about 137 mg of mannitol, about 19 mg of poloxamer, about 52 mg of polyethylene glycol, about 7 mg of hydroxyethyl cellulose, about 26 mg of crospovidone, about 3 mg of artificial vanilla flavor, about 5 mg of colloidal silicon dioxide and about 5 mg of magnesium stearate. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules.

Further provided herein are pharmaceutical compositions, comprising about 205 mg of 3-[5-(2-fluoro-phenyl)-[1,2,4]oxadiazol-3-yl]-benzoic acid or a pharmaceutically acceptable salt thereof, about 210 mg of polydextrose, about 216 mg of mannitol, about 30 mg of poloxamer, about 82 mg of polyethylene glycol, about 12 mg of hydroxyethyl cellulose, about 41 mg of crospovidone, about 6 mg of artificial vanilla flavor, about 8 mg of colloidal silicon dioxide and about 8 mg of magnesium stearate. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules.

Further provided herein are pharmaceutical compositions, comprising about 330 mg of 3-[5-(2-fluoro-phenyl)-[1,2,4]oxadiazol-3-yl]-benzoic acid or a pharmaceutically acceptable salt thereof, about 338 mg of polydextrose, about 348 mg of mannitol, about 48 mg of poloxamer, about 132 mg of polyethylene glycol, about 19 mg of hydroxyethyl cellulose, about 66 mg of crospovidone, about 9 mg of artificial vanilla flavor, about 13 mg of colloidal silicon dioxide and about 13 mg of magnesium stearate. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules.

Further provided herein are pharmaceutical compositions, comprising about 405 mg of 3-[5-(2-fluoro-phenyl)-[1,2,4]oxadiazol-3-yl]-benzoic acid or a pharmaceutically acceptable salt thereof, about 415 mg of polydextrose, about 427 mg of mannitol, about 59 mg of poloxamer, about 162 mg of polyethylene glycol, about 24 mg of hydroxyethyl cellulose, about 81 mg of crospovidone, about 12 mg of artificial vanilla flavor, about 16 mg of colloidal silicon dioxide and about 16 mg of magnesium stearate. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules.

Further provided herein are pharmaceutical compositions, comprising about 505 mg of 3-[5-(2-fluoro-phenyl)-[1,2,4]oxadiazol-3-yl]-benzoic acid or a pharmaceutically acceptable salt thereof, about 518 mg of polydextrose, about 453 mg of mannitol, about 74 mg of poloxamer, about 202 mg of polyethylene glycol, about 30 mg of hydroxyethyl cellulose, about 101 mg of crospovidone, about 15 mg of artificial vanilla flavor, about 20 mg of colloidal silicon dioxide and about 20 mg of magnesium stearate. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules.

Further provided herein are pharmaceutical compositions, comprising about 1005 mg of 3-[5-(2-fluoro-phenyl)-[1,2,4]oxadiazol-3-yl]-benzoic acid or a pharmaceutically acceptable salt thereof, about 1030 mg of polydextrose, about 901 mg of mannitol, about 147 mg of poloxamer, about 402 mg of polyethylene glycol, about 59 mg of hydroxyethyl cellulose, about 201 mg of crospovidone, about 29 mg of artificial vanilla flavor, about 39 mg of colloidal silicon dioxide and about 39 mg of magnesium stearate. In one embodiment, the pharmaceutical composition is formulated as a powder. In one embodiment, the pharmaceutical composition is formulated as a micronized powder. In one embodiment, the pharmaceutical composition is formulated as a nanoparticle. In one embodiment, the pharmaceutical composition is formulated as granules.

In certain embodiments, the unit dosage form comprises from about 35 mg to about 5,600 mg of Compound 1, from about 35 mg to about 2800 mg of Compound 1, from about 35 mg to about 1,400 mg of Compound 1, from about 125 mg to about 1,000 mg of Compound 1, from about 250 mg to about 1,000 mg of Compound 1, from about 325 mg to about 1,000 mg of Compound 1 or from about 500 mg to about 1,000 mg of Compound 1.

In certain embodiments, the unit dosage form comprises about 35 mg, about 50 mg, about 70 mg, about 100 mg, about 125 mg, about 140 mg, about 175 mg, about 200 mg, about 250 mg, about 280 mg, about 325 mg, about 350 mg, about 400 mg, about 450 mg, about 500 mg, about 560 mg, about 700 mg, about 750 mg, about 1,000 mg, about 1,400 mg, about 2800 mg or about 5600 mg of Compound 1.

In a particular embodiment, the unit dosage form comprises about 125 mg, about 250 mg or about 1,000 mg of Compound 1.

In a more particular embodiment, the unit dosage form comprises 125 mg, 250 mg or 1,000 mg of Compound 1.

In certain embodiments, the pharmaceutical composition is formulated as a powder. In one embodiment, the pharmaceutical composition is formulated as a micronized powder. In one embodiment, the pharmaceutical composition is formulated as a nanoparticle. In another embodiment, the pharmaceutical composition provided herein is formulated as granules. In certain embodiments, the pharmaceutical composition provided herein is packaged in a packet or sachet. In certain embodiments, the pharmaceutical composition provided herein is packaged in a heat-sealed laminated aluminum packet or sachet. In certain embodiments, the pharmaceutical composition provided herein is packaged in a child-resistant packet or sachet. In certain embodiments, the pharmaceutical composition provided herein is packaged in a packet or sachet, which comprises layers of polyethylene terephthalate, polyethelyene, aluminum foil, adhesive, and sealing film. In certain embodiments, the pharmaceutical composition may be provided in a bottle including, but not limited to, high density polyethylene (HDPE) bottles.

In certain embodiments, the pharmaceutical composition provided herein is formulated as granules for reconstitution. In certain embodiments, the pharmaceutical composition provided herein is formulated as granules for reconstitution as an oral suspension.

In certain embodiments, the pharmaceutical composition provided herein is reconstituted before administration by being mixed to a suspension with a pharmaceutically acceptable liquid or semi-solid solvating agent which includes, but is not limited to, water, milk, carbonated beverage, juice, fruit juice, fruit punch, applesauce, yogurt, pudding, ice cream, baby food, baby formula or a soy or grain based product.

In certain embodiments, the pharmaceutical composition provided herein is reconstituted before administration by being mixed to a suspension with water. In one embodiment, reconstitution of a 125 mg unit dosage formulation of Compound 1 is carried out by the addition of at least about 5 mL of water directly in a bottle containing Compound 1 to achieve a nominal concentration of at least about 25 mg/mL in the total volume of suspension. In another embodiment, reconstitution of a 250 mg unit dosage formulation Compound 1 is carried out by the addition of at least about 10 mL of water directly in a bottle containing Compound 1 to achieve a nominal concentration of at least about 25 mg/mL in the total volume of suspension. In another embodiment, reconstitution of a 500 mg unit dosage formulation Compound 1 is carried out by the addition of at least about 20 mL of water directly in a bottle containing Compound 1 to achieve a nominal concentration of at least about 25 mg/mL in the total volume of suspension. In another embodiment, reconstitution of a 1000 mg unit dosage formulation Compound 1 is carried out by the addition of at least about 40 mL of water directly in a bottle containing Compound 1 to achieve a nominal concentration of at least about 25 mg/mL in the total volume of suspension.

In other embodiments, a unit dosage form containing the pharmaceutical composition provided herein is only opened at the time of dose preparation. The full contents of each unit dosage form is mixed to a suspension with a liquid or a semi-solid solvating agent, wherein the liquid is at least 30 mL (1 ounce) or the semi-solid is at least 3 tablespoons. The prepared dose should be mixed well before being administered. The amount of the liquid or semi-solid solvating agent can be increased based on patient preference.

In certain embodiments, the pharmaceutical composition provided herein comprises Compound 1 as a free acid or as a pharmaceutically acceptable salt, wherein the pharmaceutically acceptable salt is a magnesium salt, a potassium salt, a sodium salt, a tromethamine salt, an L-lysine salt, an L-arginine salt, an N-methyl glucamine salt or an L-histidine salt.

5.4.3. Parenteral Formulations and Administration

The pharmaceutical compositions provided herein comprising Compound 1 can be administered parenterally by injection, infusion, or implantation, for local or systemic administration. Parenteral administration, as used herein include, without limitation, intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration including, without limitation, solutions, suspensions, emulsions, micelles, liposomes, microspheres, nanosystems and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, KS).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in the body, but allows the active ingredient in the pharmaceutical compositions to be osmotically or ionically diffused.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

5.4.4. Particle Size

In certain embodiments, the pharmaceutical compositions provided herein comprise a micronized form of Compound 1 having enhanced solubility. In certain embodiments, the pharmaceutical compositions provided herein comprise a nanoparticle form of Compound 1 having enhanced solubility and/or dissolution rate.

In specific embodiments, the pharmaceutical compositions provided herein comprise a micronized form of Compound 1 wherein >90% of the particles of Compound 1 have a diameter ($D_{90}$ value) of between about 1-10 microns having enhanced solubility. In certain embodiments, the pharmaceutical compositions provided herein comprise a micronized form of Compound 1, having a $D_{90}$ value of about 10 microns, about 9 microns, about 8 microns, about 7 microns, about 6 microns, about 5 microns, about 4 microns, about 3 microns, about 2 microns or about 1 micron having enhanced solubility. In certain embodiments, the pharmaceutical compositions provided herein comprise a micronized form of Compound 1, having a $D_{90}$ value of between about 1-5 microns having enhanced solubility and/or dissolution rate. In certain embodiments, the pharmaceutical compositions provided herein comprise a micronized form of Compound 1, having a $D_{90}$ value of about 5 microns, about 4 microns, about 3 microns, about 2 microns or about 1 micron having enhanced solubility and/or dissolution rate. In certain embodiments, the pharmaceutical compositions provided herein comprise a nanoparticle form of Compound 1 having enhanced solubility. In specific embodiments, the pharmaceutical compositions provided herein comprise a nanoparticle form of Compound 1 wherein >90% of the particles of Compound 1 have a $D_{90}$ value of about 0.1 microns, about 0.09 microns, about 0.08 microns, about 0.07 microns, about 0.06 microns, about 0.05 microns, about 0.04 microns, about 0.03 microns, about 0.02 microns or about 0.01 microns.

Provided herein are micronized forms of Compound 1 having a volume weighted mean diameter D[4,3] of from about 2 μm to about 12 μm. Also provided herein are micronized forms of Compound 1 having a surface weighted mean diameter D[3,2] of from about 1 μm to about 3 μm. Further provided herein are forms of Compound 1 having a $D_{90}$ particle size in the range of from about 5 μm to about 26 μm, having a $D_{50}$ particle size in the range of from about 1 μm to about 6 μm, or having a $D_{10}$ particle size in the range of from about 0.1 μm to about 1.5 μm.

5.4.5. Kits

The pharmaceutical compositions provided herein can be provided as an article of manufacture using packaging materials well known to those of skill in the art. Examples of pharmaceutical packaging materials include, but are not limited to, blister packs, bottles, packets, sachets, tubes, inhalers, pumps, bags, vials, containers, syringes, droppers, and any packaging material suitable for a selected formulation and intended mode of administration and treatment.

Provided herein are kits which, when used by the medical practitioner, can simplify the administration of appropriate amounts of the active ingredient to a subject. In certain embodiments, the kit provided herein includes a container and a dosage form of a pharmaceutical formulation provided herein and instructions for use thereof. In certain embodiments, the instructions included with the kit provide guidance with respect to the dosage amounts and/or dosing regimens for administration of Compound 1.

In certain embodiments, the kit includes a container comprising a dosage form of the pharmaceutical formulation provided herein, in a container comprising one or more other therapeutic agent(s) described herein. In certain embodiments the pharmaceutical formulation is provided as a white to off-white powder for oral suspension. In certain embodiments, the pharmaceutical formulation comprises a matrix and/or suspending agents, surfactants, and/or excipients. In certain embodiments the pharmaceutical formulation is provided as granules for oral suspension. In certain embodiments, the pharmaceutical formulation for oral suspension is packaged in aluminum-foil, child-resistant sachets (packets) in dose strengths containing 125, 250, or 1000 mg of the active drug substance. In certain embodiments, the kit comprises packets or sachets comprising one or more dosage strengthes of the pharmaceutical formulation for oral suspension (125, 250, or 1000 mg or matching placebo).

Kits provided herein can further include devices that are used to administer the active ingredient. Examples of such devices include, but are not limited to, syringes, needle-less injectors, drip bags, patches, droppers and inhalers.

Kits provided herein can further include pharmaceutically acceptable vehicles that can be used to administer the active ingredient. For example, if the active ingredient is provided in a solid form that must be reconstituted for parenteral administration, the kit can comprise a sealed container of a suitable vehicle in which the active ingredient can be dissolved to form a particulate-free sterile solution that is suitable for parenteral administration or can be reconstituted as a suspension for oral administration. Examples of pharmaceutically acceptable vehicles include, but are not limited to: aqueous vehicles including, but not limited to, Water for Injection USP, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol, and polypropylene glycol; and non-aqueous vehicles including, but not limited to, corn oil, cottonseed oil, peanut oil, sesame oil, ethyl oleate, isopropyl myristate, and benzyl benzoate.

5.5. Methods of Use

Provided herein are methods for treating, preventing, ameliorating or managing a nonsense mutation mediated epileptic disease, comprising administering a 1,2,4-oxadiazole benzoic acid to a patient having a nonsense mutation mediated epileptic disease. In particular, provided herein are methods for treating, preventing, ameliorating or managing a nonsense mutation mediated epileptic disease, comprising administering an effective amount of a 1,2,4-oxadiazole benzoic acid to a patient having a nonsense mutation mediated epileptic disease. Additionally provided herein are methods of treating, preventing, ameliorating or managing an epileptic disease associated with a nonsense mutation or a premature stop codon, comprising administering an effective amount of a 1,2,4-oxadiazole benzoic acid to a patient having an epileptic disease associated with a nonsense mutation or a premature stop codon.

Also provided herein are methods of treating, preventing, ameliorating or managing a nonsense mutation mediated epileptic disease by modulation of premature translation termination, comprising administering to a patient having a type of a nonsense mutation mediated epileptic disease capable of being ameliorated by modulation of premature translation termination an effective amount of a pharmaceutical composition comprising 3-[5-(2-fluoro-phenyl)-[1,2,4] oxadiazol-3-yl]benzoic acid or a salt thereof and one or more pharmaceutically acceptable carriers and excipients, as provided herein.

In certain embodiments, the administration of an effective amount of 1,2,4-oxadiazole benzoic acid to a subject results in one, two or more of the following effects in a patient having a nonsense mutation-mediated epileptic disease: (1) prevents the onset, development and/or progression of a nonsense mutation mediated epileptic disease; (2) prevents the onset, development and/or progression of one or more symptoms associated with a nonsense mutation mediated epileptic disease; (3) reduces the duration and/or severity of a nonsense mutation mediated epileptic disease; (4) reduces the number of symptoms associated with a nonsense mutation mediated epileptic disease; (5) reduces the duration of one or more symptoms associated with a nonsense mutation mediated epileptic disease; (6) reduces the severity of one or more symptoms associated with a nonsense mutation mediated epileptic disease; and (7) improves the quality of life of said subject.

In certain embodiments, the administration of an effective amount of 1,2,4-oxadiazole benzoic acid to a subject results in one, two or more of the following effects in a patient having a nonsense mutation-mediated epileptic disease, as described herein in Section 6, infra: (1) reduces the frequency of seizures from baseline, e.g., convulsive seizures, drop seizures, motor seizures, tonic-clonic seizures, hemiconvulsive seizures, drop attacks, tonic seizures, focal motor seizures, and myoclonic seizures; (2) reduces the frequency of minor seizure types, e.g., myoclonic seizures, and staring (absence or complex partial) seizures; (3) improves cognitive, motor, behavioral function, and/or qualitify of life; (4) reduces the number of episodes of status epilepticus, defined as a convulsive lasting more than 10 minutes; (5) reduces the number of uses of rescue medications; and (6) reduces the number of emergency room visits/hospitalizations.

Nonsense mutation mediated epileptic diseases to be treated in accordance with the methods described herein include, but are not limited to, Dravet syndrome, also known as Severe myoclonic epilepsy of infancy (SMEI), CDKL5, Febrile seizures (FS), Generalized epilepsy with febrile seizures plus (GEFS+), Familial temporal lobe epilepsy, Intractable childhood epilepsy, Benign familial neonatal-infantile seizures (BFNIS), Benign familial neonatal seizures (BFNIS), Juvenile myoclonic epilepsy (JME), Childhood absence epilepsy (CAE), Autosomal dominant nocturnal frontal lobe epilepsy (ADNFLE), Cryptogenic generalized epilepsy (CGE), Cryptogenic focal epilepsy (CFE), Familial focal epilepsy, Familial focal epilepsy with variable foci (FFEVF), Familial mesial temporal lobe epilepsy (FMTLE), Autosomal dominant lateral temporal epilepsy (ADLTE), Myoclonic astatic epilepsy (MAE), Severe idiopathic generalized epilepsy of infancy (SIGEI), Infantile spasms (IS), and Early-onset epileptic encephalopathy (EOEE). In certain embodiments, a patient to be treated in accordance with the methods described herein has drug-resistant epilepsy.

Symptoms of a nonsense mutation mediated epileptic disease include convulsive seizures, drop seizures, generalized unilateral (one-sided) clonic seizures or generalized tonic clonic (grand mal) seizures, characterized by unconsciousness, convulsions, and muscle rigidity; absence seizures, characterized by a short loss of consciousness; generalized myoclonic seizures, characterized by sporadic jerks, usually on both sides of the body; generalized clonic seizures, characterized by repetitive, rhythmic jerks that involve both sides of the body at the same time; generalized tonic seizures, characterized by stiffening of the muscles; generalized atonic seizures, characterized by a sudden and general loss of muscle tone, particularly in the arms and legs, which often results in a fall; simple motor partial seizures, characterized by awareness, jerking, muscle rigidity, spasms, head-turning; simple sensory partial seizures, characterized by awareness and unusual sensations affecting either the vision, hearing, smell taste, or touch; simple psychological partial seizures, characterized by awareness and memory or emotional disturbances; complex partial seizures (focal dyscognitive seizures), characterized by impairment of awareness and automatisms such as lip smacking, chewing, fidgeting, walking and other repetitive, involuntary but coordinated movements; partial seizures with secondary generalization, characterized by preservation of consciousness that then evolves into a loss of consciousness and convulsions; sudden unexpected death in epilepsy (SUDEP); and nocturnal seizures.

In some embodiments, the nonsense mutation mediated epileptic disease treated in accordance with the methods described herein results from a nonsense mutation in one or both alleles of one or more genes, including but not limited to SCN1A, CDKL5, SCN2A, GABRG2, DEPDC5, and NAPB.

In some embodiments, the nonsense mutation mediated epileptic disease treated in accordance with the methods described herein results from one or more nonsense mutations in one or both alleles of the SCN1A gene. In certain embodiments, the one or more nonsense mutations in one or both alleles of the SCN1A gene is W192X, R222X, R568X, R701X, R854X, K1017X, W1261X, R1213X, W1408X, W952X, W1284X, S219fsX275, K1100fsX1107, L1670fsX1107, and/or S1846fsX1856. In certain embodiments, the nonsense mutation mediated epileptic disease that results from a nonsense mutation in one or both alleles of SCN1A and is treated in accordance with the methods of the invention is Dravet syndrome, also known as Severe myoclonic epilepsy of infancy (SMEI). In some embodiments, a patient having Dravet syndrome that results from a W192X nonsense mutation in one or both alleles of the SCN1A gene is treated in accordance with the methods of the invention. In some embodiments, a patient having Dravet syndrome that results from a R222X nonsense mutation in one or both alleles of the SCN1A gene is treated in accordance with the methods of the invention. In some embodiments, a patient having Dravet syndrome that results from a R568X nonsense mutation in one or both alleles of the SCN1A gene is treated in accordance with the methods of the invention. In some embodiments, a patient having Dravet syndrome that results from a R701X nonsense mutation in one or both alleles of the SCN1A gene is treated in accordance with the methods of the invention. In some embodiments, a patient having Dravet syndrome that results from a R854X nonsense mutation in one or both alleles of the SCN1A gene is treated in accordance with the methods of the invention. In some embodiments, a patient having Dravet syndrome that results from a L1017X nonsense mutation in one or both alleles of the SCN1A gene is treated in accordance with the methods of the invention. In some embodiments, a patient having Dravet syndrome that results from a W1261X nonsense mutation in one or both alleles of the SCN1A gene is treated in accordance with the methods of the invention. In some embodiments, a patient having Dravet syndrome that results from a R1213X nonsense mutation in one or both alleles of the SCN1A gene is treated in accordance with the methods of the invention. In some embodiments, a patient having Dravet syndrome that results from a W1408X nonsense mutation in one or both alleles of the SCN1A gene is treated in accordance with the methods of the invention. In some embodiments, a patient having Dravet syndrome that results from a W952X nonsense mutation in one or both alleles of the SCN1A gene is treated in accordance with the methods of the invention. In some embodiments, a patient having Dravet syndrome that results from a W1284X nonsense mutation in one or both alleles of the SCN1A gene is treated in accordance with the methods of the invention. In some embodiments, a patient having Dravet syndrome that results from a S219fsX275 nonsense mutation in one or both alleles of the SCN1A gene is treated in accordance with the methods of the invention. In some embodiments, a patient having Dravet syndrome that results from a K1100fsX1107 nonsense mutation in one or both alleles of the SCN1A gene is treated in accordance with the methods of the invention. In some embodiments, a patient having Dravet syndrome that results from a L1670fsX1107 nonsense mutation in one or both alleles of the SCN1A gene is treated in accordance with the methods of the invention. In some embodiments, a patient having Dravet syndrome that results from a S1846fsX1856 nonsense mutation in one or both alleles of the SCN1A gene is treated in accordance with the methods of the invention.

In some embodiments, the nonsense mutation mediated epileptic disease treated in accordance with the methods described herein results from one or more nonsense mutations in one or both alleles of the CDKL5 gene. In certain embodiments, the one or more nonsense mutations in one or both alleles of the CDKL5 gene is R59X, R550X, Q834X, R79X, Q118X, R134X, L142X, Q347X, R559X, and/or R970X. In certain embodiments, the nonsense mutation mediated epileptic disease that results from a nonsense mutation in one or both alleles of CDKL5 and is treated in accordance with the methods of the invention is CDKL5. In some embodiments, CDKL5 that results from a R59X nonsense mutation in one or both alleles of the CDKL5 gene is the nonsense mutation mediated epileptic disease treated in accordance with the methods of the invention. In some embodiments, CDKL5 that results from a R550X nonsense mutation in one or both alleles of the CDKL5 gene is the nonsense mutation mediated epileptic disease treated in accordance with the methods of the invention. In some embodiments, CDKL5 that results from a Q834X nonsense mutation in one or both alleles of the CDKL5 gene is the nonsense mutation mediated epileptic disease treated in accordance with the methods of the invention. In some embodiments, CDKL5 that results from a R79X nonsense mutation in one or both alleles of the CDKL5 gene is the nonsense mutation mediated epileptic disease treated in accordance with the methods of the invention. In some embodiments, CDKL5 that results from a Q118X nonsense mutation in one or both alleles of the CDKL5 gene is the nonsense mutation mediated epileptic disease treated in accordance with the methods of the invention. In some embodiments, CDKL5 that results from a R134X nonsense mutation in one or both alleles of the CDKL5 gene is the nonsense mutation mediated epileptic disease treated in accordance with the methods of the invention. In some embodiments, CDKL5 that results from a L142X nonsense mutation in one or both alleles of the CDKL5 gene is the nonsense mutation mediated epileptic disease treated in accordance with the methods of the invention. In some embodiments, CDKL5 that results from a Q347X nonsense mutation in one or both alleles of the CDKL5 gene is the nonsense mutation mediated epileptic disease treated in accordance with the methods of the invention. In some embodiments, CDKL5 that results from a R559X nonsense mutation in one or both alleles of the CDKL5 gene is the nonsense mutation mediated epileptic disease treated in accordance with the methods of the invention. In some embodiments, CDKL5 that results from a R970X nonsense mutation in one or both alleles of the CDKL5 gene is the nonsense mutation mediated epileptic disease treated in accordance with the methods of the invention. In some embodiments, a patient having CDKL5 that results from a R59X nonsense mutation in one or both alleles of the CDKL5 gene is treated in accordance with the methods of the invention. In some embodiments, a patient having CDKL5 that results from a R550X nonsense mutation in one or both alleles of the CDKL5 gene is treated in accordance with the methods of the invention. In some embodiments, a patient having CDKL5 that results from a Q834X nonsense mutation in one or both alleles of the CDKL5 gene is treated in accordance with the methods of the invention. In some embodiments, a patient having CDKL5 that results from a R79X nonsense mutation in one or both alleles of the CDKL5 gene is treated in accordance with the methods of the invention. In some embodiments, a patient having CDKL5 that results from a Q118X nonsense mutation in one or both alleles of the CDKL5 gene is treated in accordance with the methods of the invention. In some embodiments, a patient having CDKL5 that results from a R134X nonsense mutation in one or both alleles of the CDKL5 gene is treated in accordance with the methods of the invention. In some embodiments, a patient having CDKL5 that results from a L142X nonsense mutation in one or both alleles of the CDKL5 gene is treated in accordance with the methods of the invention. In some embodiments, a patient having CDKL5 that results from a Q347X nonsense mutation in one or both alleles of the CDKL5 gene is treated in accordance with the methods of the invention. In some embodiments, a patient having CDKL5 that results from a R559X nonsense mutation in one or both alleles of the CDKL5 gene is treated in accordance with the methods of the invention. In some embodiments, a patient having CDKL5 that results from a R970X nonsense mutation in one or both alleles of the CDKL5 gene is treated in accordance with the methods of the invention.

In some embodiments, the nonsense mutation mediated epileptic disease treated in accordance with the methods described herein results from one or more nonsense mutations in one or both alleles of the SCN2A gene. In certain embodiments, the one or more nonsense mutations in one or both alleles of the SCN2A gene is R102X. In certain embodiments, the nonsense mutation mediated epileptic disease that results from a nonsense mutation in one or both alleles of the SCN2A and is treated in accordance with the methods of the invention is Intractable Childhood Epilepsy. In some embodiments, a patient having Intractable Childhood Epilepsy that results from a R102X nonsense mutation in one or both alleles of the SCN2A gene is treated in accordance with the methods of the invention.

In some embodiments, the nonsense mutation mediated epileptic disease treated in accordance with the methods described herein results from one or more nonsense mutations in one or both alleles of the GABRG2 gene. In certain embodiments, the one or more nonsense mutations in one or both alleles of the GABRG2 gene is R136X, W429X, Q40X, Q390X, Q1X, Q351X, W390X and/or Y444Mfs51X. In certain embodiments, the nonsense mutation mediated epileptic disease that results from a nonsense mutation in one or both alleles of GABRG2 and is treated in accordance with the methods of the invention is Generalized Epilepsy with Febrile Seizures plus (GEFS+), Dravet syndrome, or Febrile Seizures (FS). In some embodiments, a patient having a nonsense mutation mediated epileptic disease that results from a R136X nonsense mutation in one or both alleles of the GABRG2 gene is treated in accordance with the methods of the invention. In some embodiments, a patient having a nonsense mutation mediated epileptic disease that results from a W429X nonsense mutation in one or both alleles of the GABRG2 gene is treated in accordance with the methods of the invention. In some embodiments, a patient having a nonsense mutation mediated epileptic disease that results from a Q40X nonsense mutation in one or both alleles of the GABRG2 gene is treated in accordance with the methods of the invention. In some embodiments, a patient having a nonsense mutation mediated epileptic disease that results from a Q390X nonsense mutation in one or both alleles of the GABRG2 gene is treated in accordance with the methods of the invention. In some embodiments, a patient having a nonsense mutation mediated epileptic disease that results from a Q1X nonsense mutation in one or both alleles of the GABRG2 gene is treated in accordance with the methods of the invention. In some embodiments, a patient having a nonsense mutation mediated epileptic disease that results from a Q351X nonsense mutation in one or both alleles of the GABRG2 gene is treated in accordance with the methods of the invention. In some embodiments, a patient having a nonsense mutation mediated epileptic disease that results from a W390X nonsense mutation in one or both alleles of the GABRG2 gene is treated in accordance with the methods of the invention. In some embodiments, a patient having a nonsense mutation mediated epileptic disease that results from a Y444Mfs51X nonsense mutation in one or both alleles of the GABRG2 gene is treated in accordance with the methods of the invention.

In some embodiments, the nonsense mutation mediated epileptic disease treated in accordance with the methods described herein results from one or more nonsense mutations in one or both alleles of the DEPDC5 gene. In certain embodiments, the one or more nonsense mutations in one or both alleles of the DEPDC5 gene is R555X and/or Y306X. In certain embodiments, the nonsense mutation mediated epileptic disease that results from a nonsense mutation in one or both alleles of DEPDC5 and is treated in accordance with the methods of the invention is Familial Focal Epilepsy, Familial Focal Epilepsy with Variable Foci (FFEVF), Familial Mesial Temporal Lobe Epilepsy (FMTLE), or Autosomal Dominant Lateral Temporal Epilepsy (ADLTE). In some embodiments, a patient having a nonsense mutation mediated epileptic disease that results from a R555X nonsense mutation in one or both alleles of the DEPDC5 gene is treated in accordance with the methods of the invention. In some embodiments, a patient having a nonsense mutation mediated epileptic disease that results from a Y306X nonsense mutation in one or both alleles of the DEPDC5 gene is treated in accordance with the methods of the invention.

In some embodiments, the nonsense mutation mediated epileptic disease treated in accordance with the methods described herein results from one or more nonsense mutations in one or both alleles of the NAPB gene. In certain embodiments, the one or more nonsense mutations in one or both alleles of the NAPB gene is S160X. In certain embodiments, the nonsense mutation mediated epileptic disease that results from a nonsense mutation in one or both alleles of the NAPB and is treated in accordance with the methods of the invention is Early-Onset Epileptic Encephalopathy (EOEE). In some embodiments, a patient having a nonsense mutation mediated epileptic disease that results from a S160X nonsense mutation in one or both alleles of the NAPB gene is treated in accordance with the methods of the invention.

Further provided herein are methods for treating, preventing, ameliorating or managing a symptom of a nonsense mutation mediated epileptic disease by modulation of premature translation termination, comprising administering to a patient having a symptom of a nonsense mutation mediated epileptic disease capable of being ameliorated by modulation of premature translation termination an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein.

Further provided herein are methods for treating, preventing, ameliorating or managing a CDKL5 related epilepsy, comprising administering to a patient having the CDKL5 related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. Further provided herein are methods for treating, preventing, ameliorating or managing a symptom of the CDKL5 related epilepsy, comprising administering to a patient having a symptom of the CDKL5 related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. In certain embodiments, the CDKL5 related epilepsy results from certain mutations on one or both alleles of the CDKL5 gene. In certain embodiments, the CDKL5 related epilepsy results from a R59X nonsense mutation on one or both alleles of the CDKL5 gene. In certain embodiments, the CDKL5 related epilepsy results from a R550X nonsense mutation on one or both alleles of the CDKL5 gene. In certain embodiments, the CDKL5 related epilepsy results from a Q834X nonsense mutation on one or both alleles of the CDKL5 gene. In certain embodiments, the CDKL5 related epilepsy results from a R79X nonsense mutation on one or both alleles of the CDKL5 gene. In certain embodiments, the CDKL5 related epilepsy results from a Q118X nonsense mutation on one or both alleles of the CDKL5 gene. In certain embodiments, the CDKL5 related epilepsy results from a R134X nonsense mutation on one or both alleles of the CDKL5 gene. In certain embodiments, the CDKL5 related epilepsy results from a L142X nonsense mutation on one or both alleles of the CDKL5 gene. In certain embodiments, the CDKL5 related epilepsy results from a Q347X nonsense mutation on one or both alleles of the CDKL5 gene. In certain embodiments, the CDKL5 related epilepsy results from a R559X nonsense mutation on one or both alleles of the CDKL5 gene. In certain embodiments, the CDKL5 related epilepsy results from a R970X nonsense mutation on one or both alleles of the CDKL5 gene.

Further provided herein are methods for treating, preventing, ameliorating or managing a SCN1A related epilepsy, comprising administering to a patient having the SCN1A related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. Further provided herein are methods for treating, preventing, ameliorating or managing a symptom of the SCN1A related epilepsy, comprising administering to a patient having a symptom of the SCN1A related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. In certain embodiments, the SCN1A related epilepsy results from certain mutations on one or both alleles of the SCN1A gene.

Further provided herein are methods for treating, preventing, ameliorating or managing a SCN1A related epilepsy such as Dravet syndrome. Also provided herein are methods for treating, preventing, ameliorating or managing Dravet syndrome, comprising administering to a patient having Dravet syndrome an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. Further provided herein are methods for treating, preventing, ameliorating or managing a symptom of Dravet syndrome, comprising administering to a patient having a symptom of Dravet syndrome an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. In certain embodiments, Dravet syndrome results from certain mutations on one or both alleles of the SCN1A gene. In certain embodiments, Dravet syndrome results from a W192X nonsense mutation on one or both alleles of the SCN1A gene.

Further provided herein are methods for treating, preventing, ameliorating or managing a SCN2A related epilepsy, comprising administering to a patient having the SCN2A related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. Further provided herein are methods for treating, preventing, ameliorating or managing a symptom of the SCN2A related epilepsy, comprising administering to a patient having a symptom of the SCN2A related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. In certain embodiments, the SCN2A related epilepsy results from certain mutations on one or both alleles of the SCN2A gene. In certain embodiments, the SCN2A related epilepsy results from a R102X nonsense mutation on one or both alleles of the SCN2A gene.

Further provided herein are methods for treating, preventing, ameliorating or managing a GABRG2 related epilepsy, comprising administering to a patient having the GABRG2 related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. Further provided herein are methods for treating, preventing, ameliorating or managing a symptom of the GABRG2 related epilepsy, comprising administering to a patient having a symptom of the GABRG2 related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. In certain embodiments, the GABRG2 related epilepsy results from certain mutations on one or both alleles of the GABRG2 gene. In certain embodiments, the GABRG2 related epilepsy results from a R136X nonsense mutation on one or both alleles of the GABRG2 gene. In certain embodiments, the GABRG2 related epilepsy results from a W429X nonsense mutation on one or both alleles of the GABRG2 gene. In certain embodiments, the GABRG2 related epilepsy results from a Q40X nonsense mutation on one or both alleles of the GABRG2 gene. In certain embodiments, the GABRG2 related epilepsy results from a Q390X nonsense mutation on one or both alleles of the GABRG2 gene. In certain embodiments, the GABRG2 related epilepsy results from a Q1X nonsense mutation on one or both alleles of the GABRG2 gene. In certain embodiments, the GABRG2 related epilepsy results from a Q351X nonsense mutation on one or both alleles of the GABRG2 gene. In certain embodiments, the GABRG2 related epilepsy results from a W390X nonsense mutation on one or both alleles of the GABRG2 gene. In certain embodiments, the GABRG2 related epilepsy results from a Y444Mfs51X nonsense mutation on one or both alleles of the GABRG2 gene.

Further provided herein are methods for treating, preventing, ameliorating or managing a DEPDC5 related epilepsy, comprising administering to a patient having the DEPDC5 related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. Further provided herein are methods for treating, preventing, ameliorating or managing a symptom of the DEPDC5 related epilepsy, comprising administering to a patient having a symptom of the DEPDC5 related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. In certain embodiments, the DEPDC5 related epilepsy results from certain mutations on one or both alleles of the DEPDC5 gene. In certain embodiments, the DEPDC5 related epilepsy results from a R555X nonsense mutation on one or both alleles of the DEPDC5 gene. In certain embodiments, the DEPDC5 related epilepsy results from a Y306X nonsense mutation on one or both alleles of the DEPDC5 gene.

Further provided herein are methods for treating, preventing, ameliorating or managing a NAPB related epilepsy, comprising administering to a patient having the NAPB related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. Further provided herein are methods for treating, preventing, ameliorating or managing a symptom of the NAPB related epilepsy, comprising administering to a patient having a symptom of the NAPB related epilepsy an effective amount of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein. In certain embodiments, the NAPB related epilepsy results from certain mutations on one or both alleles of the NAPB gene. In certain embodiments, the NAPB related epilepsy results from a S160X nonsense mutation on one or both alleles of the NAPB gene.

Also provided herein are methods of screening subjects having a nonsense mutation mediated epileptic disease or one or more symptoms of a nonsense mutation mediated epileptic disease for the presence of a nonsense mutation, and when a nonsense mutation is identified, an effective amount of a pharmaceutical composition comprising an effective amount of 3-[5-(2-fluoro-phenyl)-[1,2,4]oxadiazol-3-yl]benzoic acid or a salt thereof provided herein can be administered to the patient to prevent the onset, recurrence, spread or worsening of the disease or a symptom thereof. Methods of screening subjects for the presence of a nonsense mutation include whole-exome sequencing of a sample obtained from a patient. In certain embodiments, it has been determined through screening that the subject possesses a nonsense mutation. In certain embodiments, it has been determined through screening which premature stop codon the patient has (i.e., UAA, UGA, or UAG).

In certain embodiments, a patient treated in accordance with the methods provided herein is as described herein at Section 6, infra.

In certain embodiments, a patient treated in accordance with the methods provided herein is two years old. In certain embodiments, a patient treated in accordance with the methods provided herein is more than two years old. In certain embodiments, a patient treated in accordance with the methods provided herein is less than twelve years old. In certain embodiments, a patient treated in accordance with the methods provided herein is twelve years old. In certain embodiments, a patient treated in accordance with the methods provided herein is two-twelve years old.

In certain embodiments, a patient treated in accordance with the methods provided herein has been diagnosed with a nonsense mutation in one or more alleles for SCN1A deficiency (in particular, Dravet syndrome). In certain embodiments, a patient treated in accordance with the methods provided herein has been diagnosed with a nonsense mutation in one or more alleles for CDKL5 deficiency. In certain embodiments, a patient treated in accordance with the methods provided herein has been diagnosed with a nonsense mutation in one or more alleles for SCN2A deficiency. In certain embodiments, a patient treated in accordance with the methods provided herein has been diagnosed with a nonsense mutation in one or more alleles for GABRG2 deficiency. In certain embodiments, a patient treated in accordance with the methods provided herein has been diagnosed with a nonsense mutation in one or more alleles for DEPDC5 deficiency. In certain embodiments, a patient treated in accordance with the methods provided herein has been diagnosed with a nonsense mutation in one or more alleles for NAPB deficiency.

In certain embodiments, a patient treated in accordance with the methods provided herein has drug-resistant epilepsy. In certain embodiments, a patient treated in accordance with the methods provided herein is refractory to treatment with or more antiepileptic drugs. In certain embodiments, a patient treated in accordance with the methods provided herein is refractory to treatment with one or more of the following antiepileptic drugs: Valproic acid, Divalproex sodium, Phenytoin, Primidone, Phenobarbital, Carbamazepine, Diazepam, Clonazepam, Ethosuximide, Eslicarbazepine, Felbamate, Perampanel, Tiagabine, Topiramate, Levetiracetam, and/or Lamotrigine.

In certain embodiments, the methods provided herein comprise the administration of a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, in three doses in a 24 hour period according to the formula: 1X, 1X, 2X, where X is a particular dose (e.g., 2 mg/kg, 5 mg/kg, 8 mg/kg, 10 mg/kg, 15 mg/kg or 20 mg/kg) of the active agent. In a specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period for a plurality of 24 hour periods at doses of about 1 mg/kg to about 3 mg/kg (e.g., about 2 mg/kg), about 3 mg/kg to about 7 mg/kg (e.g., about 5 mg/kg), about 6 mg/kg to about 10 mg/kg (e.g., about 8 mg/kg), about 7 mg/kg to about 13 mg/kg (e.g., about 10 mg/kg), about 13 mg/kg to about 17 mg/kg (e.g., about 15 mg/kg), or about 18 mg/kg to about 22 mg/kg (e.g., about 20 mg/kg) of 3-[5-(2-fluoro-phenyl)-[1,2,4]oxadiazol-3-yl]benzoic acid or a salt thereof and one or more pharmaceutically acceptable carriers and excipients, as provided herein, for a plurality of 24 hour periods including, but not limited to, days, weeks, months or years. In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of about 5 mg/kg to about 9 mg/kg (e.g., about 7 mg/kg), about 5 mg/kg to about 9 mg/kg (e.g., about 7 mg/kg) and 12 mg/kg to about 16 mg/kg (e.g., about 14 mg/kg) of the active agent for weeks, months or years. In a specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of about 8 mg/kg to about 12 mg/kg (e.g., about 10 mg/kg), about 8 mg/kg to about 12 mg/kg (e.g., about 10 mg/kg) and about 18 mg/kg to about 22 mg/kg (e.g., about 20 mg/kg) of the active agent for days, weeks, months or years. In a specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of about 18 mg/kg to about 22 mg/kg (e.g., about 20 mg/kg), about 18 mg/kg to about 22 mg/kg (e.g., about 20 mg/kg) and about 38 mg/kg to about 42 mg/kg (e.g., about 40 mg/kg) of the active agent for days, weeks, months or years. In each 24 hour period that the active agent is administered, it is preferably administered three times at approximately 6-, 6, and 12-hour intervals (e.g., at ~7:00 AM after breakfast, ~1:00 PM after lunch, and at ~7:00 PM after supper).

In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 2 mg/kg, 2 mg/kg, and 4 mg/kg of the active agent for days, weeks, months or years. In each 24 hour period that the active agent is administered, it is preferably administered three times at approximately 6-, 6, and 12-hour intervals (e.g., at ~7:00 AM after breakfast, ~1:00 PM after lunch, and at ~7:00 PM after supper). In another specific embodiment, a pharmaceutical composition comprising 3-[5-(2-fluoro-phenyl)-[1,2,4]oxadiazol-3-yl] benzoic acid or a salt thereof and one or more pharmaceutically acceptable carriers and excipients, as provided herein, is continuously administered three times per 24 hour period at doses of 2 mg/kg in the morning, 2 mg/kg at midday, and 4 mg/kg in the evening for days, weeks, months or years. In yet another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 2 mg/kg in the morning, 2 mg/kg at midday, and 4 mg/kg in the evening for 12 weeks.

In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 5 mg/kg, 5 mg/kg, and 10 mg/kg of the active agent for days, weeks, months or years. In each 24 hour period that the active agent is administered, it is preferably administered three times at approximately 6-, 6, and 12-hour intervals (e.g., at ~7:00 AM after breakfast, ~1:00 PM after lunch, and at ~7:00 PM after supper). In another specific embodiment, a pharmaceutical composition comprising 3-[5-(2-fluoro-phenyl)-[1,2,4]oxadiazol-3-yl] benzoic acid or a salt thereof and one or more pharmaceutically acceptable carriers and excipients, as provided herein, is continuously administered three times per 24 hour period at doses of 5 mg/kg in the morning, 5 mg/kg at midday, and 10 mg/kg in the evening for days, weeks, months or years. In yet another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 5 mg/kg in the morning, 5 mg/kg at midday, and 10 mg/kg in the evening for 12 weeks.

In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 8 mg/kg, 8 mg/kg, and 16 mg/kg of the active agent for days, weeks, months or years. In each 24 hour period that the active agent is administered, it is preferably administered three times at approximately 6-, 6, and 12-hour intervals (e.g., at ~7:00 AM after breakfast, ~1:00 PM after lunch, and at ~7:00 PM after supper). In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 8 mg/kg in the morning, 8 mg/kg at midday, and 16 mg/kg in the evening for days, weeks, months or years. In yet another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 8 mg/kg in the morning, 8 mg/kg at midday, and 16 mg/kg in the evening for 12 weeks.

In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 10 mg/kg, 10 mg/kg, and 20 mg/kg of the active agent for days, weeks, months or years. In each 24 hour period that the active agent is administered, it is preferably administered three times at approximately 6-, 6, and 12-hour intervals (e.g., at ~7:00 AM after breakfast, ~1:00 PM after lunch, and at ~7:00 PM after supper). In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 10 mg/kg in the morning, 10 mg/kg at midday, and 20 mg/kg in the evening for days, weeks, months or years. In yet another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 10 mg/kg in the morning, 10 mg/kg at midday, and 20 mg/kg in the evening for 12 weeks.

In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 15 mg/kg, 15 mg/kg, and 30 mg/kg of the active agent for days, weeks, months or years. In each 24 hour period that the active agent is administered, it is preferably administered three times at approximately 6-, 6, and 12-hour intervals (e.g., at ~7:00 AM after breakfast, ~1:00 PM after lunch, and at ~7:00 PM after supper). In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 15 mg/kg in the morning, 15 mg/kg at midday, and 30 mg/kg in the evening for days, weeks, months or years. In yet another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 15 mg/kg in the morning, 15 mg/kg at midday, and 30 mg/kg in the evening for 12 weeks.

In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 20 mg/kg, 20 mg/kg, and 40 mg/kg of the active agent for days, weeks, months or years. In each 24 hour period that the active agent is administered, it is preferably administered three times at approximately 6-, 6, and 12-hour intervals (e.g., at ~7:00 AM after breakfast, ~1:00 PM after lunch, and at ~7:00 PM after supper). In another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 20 mg/kg in the morning, 20 mg/kg at midday, and 40 mg/kg in the evening for days, weeks, months or years. In yet another specific embodiment, a pharmaceutical composition comprising 3-[5-(2-fluoro-phenyl)-[1,2,4]oxadiazol-3-yl]benzoic acid or a salt thereof and one or more pharmaceutically acceptable carriers and excipients, as provided herein, is continuously administered three times per 24 hour period at doses of 20 mg/kg in the morning, 20 mg/kg at midday, and 40 mg/kg in the evening for 12 weeks.

In specific embodiments, a pharmaceutical composition provided herein is administered to a patent in accordance with the treatment regimen provided herein at Section 6, infra.

Compound 1 therapeutic efficacy follows a bell-shaped dose-response curve, wherein achieving and maintaining a certain steady-state plasma concentration within a particular range results in maximal activity. Thus, it is believed that individual patients may require particular dosage amounts (i.e., 1X, 1X, 2X, where X is a particular dose such as 2 mg/kg, 5 mg/kg, 8 mg/kg, 10 mg/kg, 15 mg/kg or 20 mg/kg) in order to achieve a therapeutically effective plasma concentration of Compound 1.

In certain embodiments, the methods provided herein comprise maintaining a plasma concentration of Compound 1 of greater than: about 0.1 µg/mL, about 0.5 µg/mL, about 2 µg/mL, about 5 µg/mL, about 10 µg/mL, about 20 µg/mL, about 25 µg/mL, about 40 µg/mL, about 50 µg/mL, about 100 µg/mL, about 150 µg/mL, about 200 µg/mL, about 250 µg/mL or about 500 µg/mL in a patient for at least about 2, 2.5, 3, 3.5, 4, 4.5, 5, 6, 8, 12 or 24 hours or longer. Levels of Compound 1 in plasma can be measured, for example, by high performance liquid chromatography (HPLC).

In another embodiment, the methods provided herein comprise maintaining a plasma concentration of Compound 1 of about 0.1 µg/mL to about 500 µg/mL, about 2 µg/mL to about 40 µg/mL, about 2 µg/mL to about 20 µg/mL, about 2 µg/mL to about 10 µg/mL or about 10 µg/mL to about 20 µg/mL in a patient for at least about 2, 2.5, 3, 3.5, 4, 4.5, 5, 6, 8, 12 or 24 hours or longer.

In some embodiments, Compound 1 is administered in combination with at least one additional therapeutic agent. In some embodiments, the additional therapeutic agent is administered before administration of Compound 1, after administration of Compound 1, simultaneously with administration of Compound 1, or a combination thereof. In some embodiments, the additional therapeutic agent is laronidase (more specifically, α-L-iduronidase) and/or one or more anti-histamine(s).

In certain embodiments, Compound 1 is used in combination with one or more therapies to treat a nonsense mutation mediated epileptic disease. In a specific embodiment, the one or more therapies used for the treatment, prevention, amelioration or management of a nonsense mutation mediated epileptic disease in combination with Compound 1 or a pharmaceutical composition provided herein are anticonvulsant drug(s). In a specific embodiment, the one or more therapies used for the treatment, prevention, amelioration or management of a nonsense mutation mediated epileptic disease in combination with Compound 1 or a pharmaceutical composition provided herein are Valproic acid, Divalproex sodium, Phenytoin, Primidone, Phenobarbital, Carbamazepine, Diazepam, Clonazepam, Ethosuximide, Eslicarbazepine, Felbamate, Perampanel, Tiagabine, Topiramate, Levetiracetam, and/or Lamotrigine.

It will be understood that the amounts of a pharmaceutical composition or active agent administered to a patient in need thereof are or can be calculated based upon the actual weight of the patient in question or the average weight of the patient population in question (e.g., male or female, including adults and children).

6. EXAMPLES

6.1. Ataluren Promotes Concentration-Dependent Readthrough Premature Stop Codons in SCN1A and CDKL5 mRNA Sequences.

Figure 2:
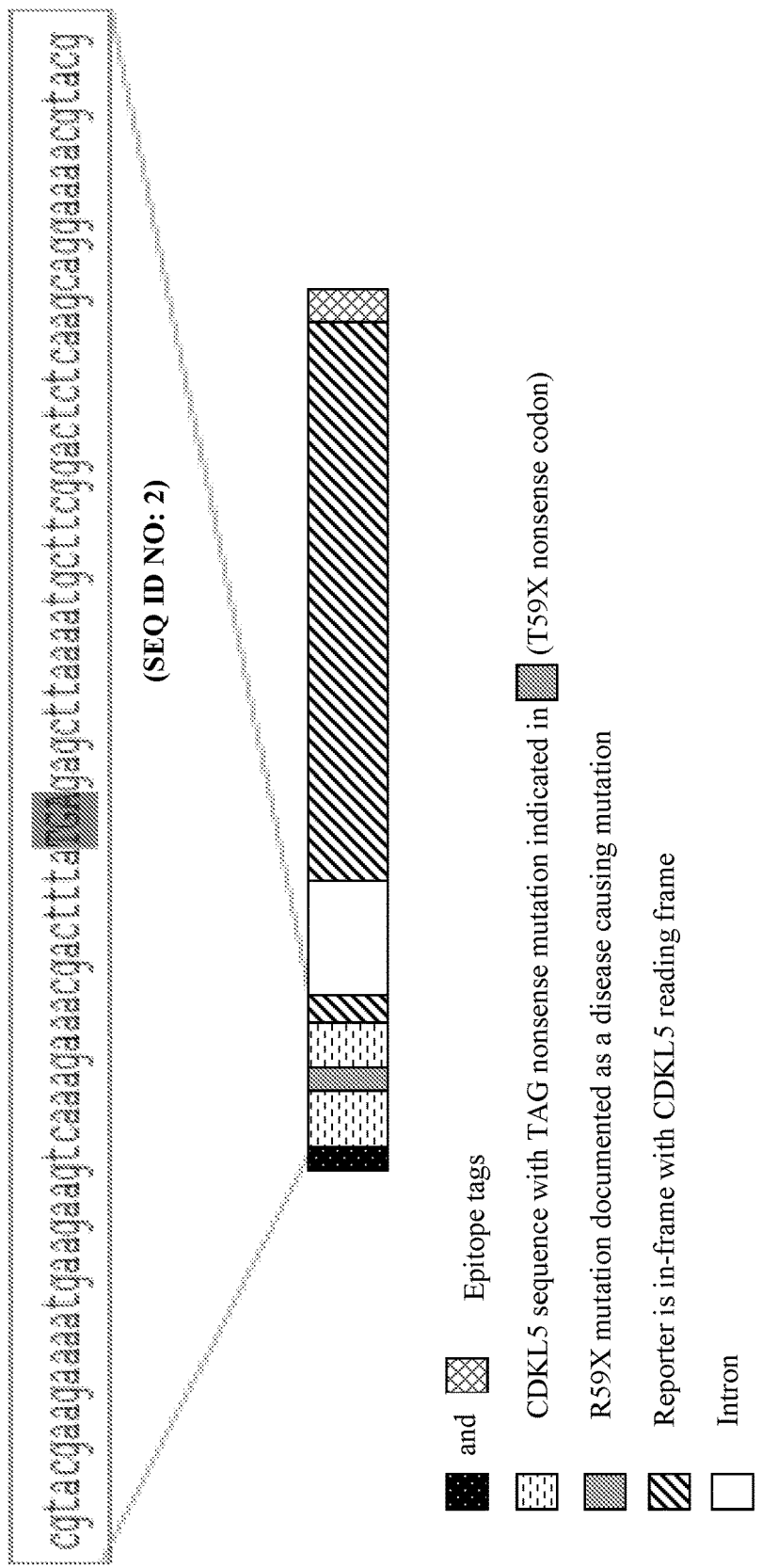
FIG. 2 is a schematic showing the reporter construct used to monitor readthrough activity of CDKL5 nonsense codon R59X. The CDKL5 nucleotide sequence used in the reporter construct is shown (SEQ ID NO: 2) with the TGA nonsense mutation (R59X) indicated by gray shading.
Figure 3:
FIG. 3 is a schematic showing the reporter construct used to monitor readthrough activity of CDKL5 nonsense codon (R550X). The CDKL5 nucleotide sequence used in the reporter construct is shown (SEQ ID NO: 3) with the TGA nonsense mutation (R550X) indicated by gray shading.

Luciferase reporter constructs were generated to evaluate readthrough activity of compounds at premature stop codons present in SCN1A and CDKL5 mRNA sequences. FIG. 1 is a schematic of the reporter construct used to monitor readthrough activity of SCN1A nonsense mutation W192X (UAG premature stop). FIG. 2 is a schematic of the reporter construct used to monitor readthrough activity of CDKL5 nonsense mutation R59X (UGA premature stop). FIG. 3 is a schematic of the reporter construct used to monitor readthrough activity of CDKL5 nonsense mutation R550X (UGA premature stop). In each of the constructs, luciferase reporter is flanked by a 3XHA epitope tag at the amino-terminus and a FLAG epitope tag at the C-terminus. An intron from the TPI gene was inserted in the luciferase gene. Sequences from SCN1A (see FIG. 1) and CDKL5 (see FIGS. 2 and 3) harboring disease-associated nonsense mutations were introduced in-frame with the reporter sequence such that readthrough at the premature stop codon results in the production of a functional luciferase protein.

Figure 4:
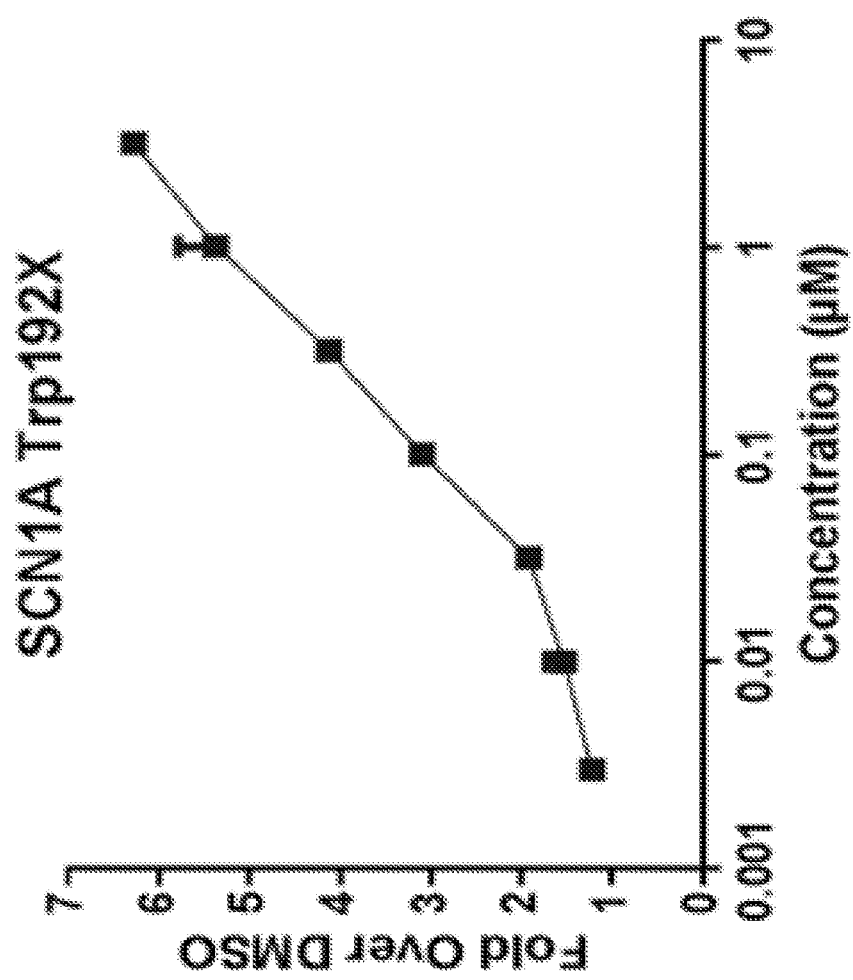
FIG. 4 is a graph showing the fold increase in readthrough activity of a 1,2,4-oxadiazole benzoic acid compound, specifically, 3-[5-(2-fluoro-phenyl)-[1,2,4]oxadiazol-3-yl]-benzoic acid, compared to DMSO in cells harboring the SCN1A reporter construct shown in FIG. 1.
Figure 5:
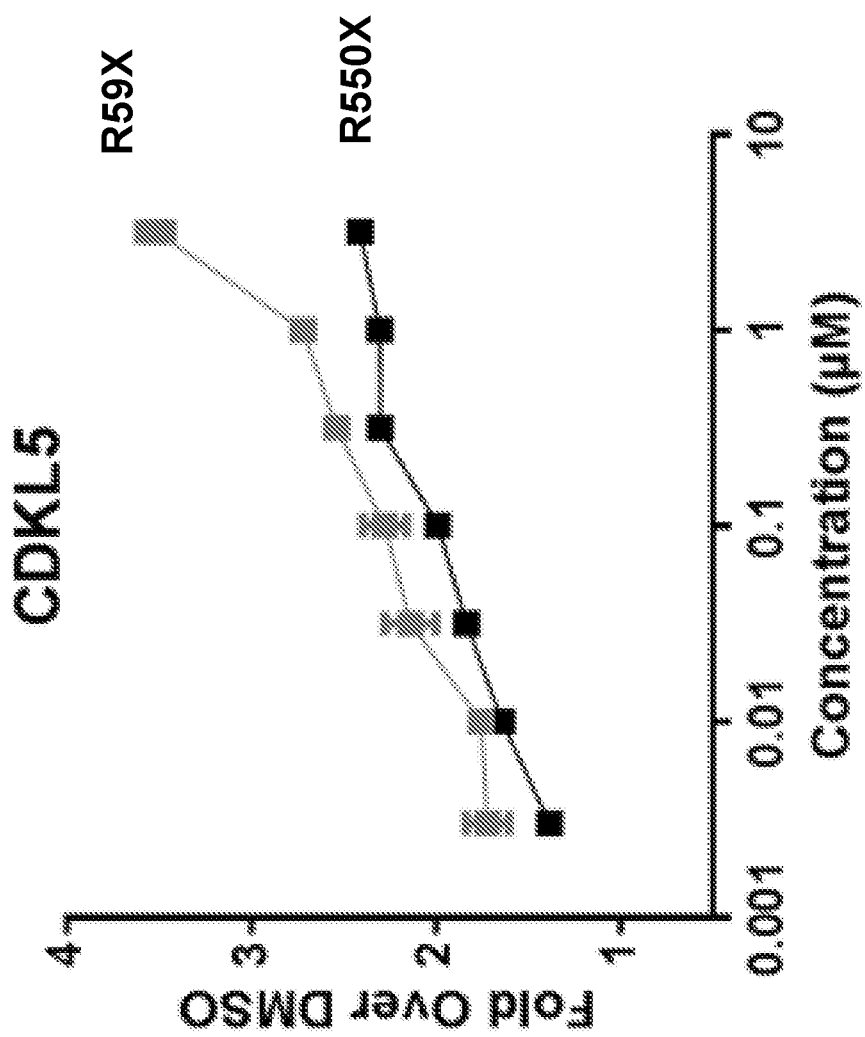
FIG. 5 is a graph showing the fold increase in readthrough activity of a 1,2,4-oxadiazole benzoic acid compound, specifically, 3-[5-(2-fluoro-phenyl)-[1,2,4]oxadiazol-3-yl]-benzoic acid, compared to DMSO in cells harboring the CDKL5 reporter constructs shown in FIG. 2 (R59X) and FIG. 3 (R550X).

293H cells were transfected with either construct SCN1A-Trp192x (FIG. 1), construct CDKL5-R59X (FIG. 2), or construct CDKL5-R550X (FIG. 3). The cells were treated with solvent (DMSO) or 3-[5-(2-fluoro-phenyl)-[1,2,4]oxadiazol-3-yl]benzoic acid (ataluren) (decreasing concentrations, starting at 3 uM) for 24 hours. The ability of ataluren to promote readthrough at the premature stop codon in each of the constructs was measured and reported as the relative light units (y-axis). The results are shown in FIG. 4 (SCN1A) and FIG. 5 (CDKL5). The results demonstrate that ataluren promotes concentration-dependent readthrough of premature stop codons inserted in sequences from the SCN1A and CDKL5 mRNA.

6.2. Protocol for a Phase 2 Randomized, Double-blind Placebo-controlled Cross-over Safety and Tolerability Study of Ataluren for Drug-resistant Epilepsy in Patients with Nonsense Mutation CDKL5 or Dravet Syndrome This Example describes a clinical research protocol for a human research study. This study is conducted in accordance with the protocol, United States (US) government research regulations, and applicable international standards of Good Clinical Practice (GCP), and institutional research policies and procedures. See Table 1 below for a synopsis of the clinical protocol. See Table 2 below for a List of Abbreviations.

TABLE 1

Clinical Protocol Synopsis

| | |
|---|---|
| Phase: | Phase 2 |
| Methodology: | Interventional study |
| Study Duration: | 32 weeks with extension available |
| Objectives: | The primary objective of this study is to: Characterize the safety profile of ataluren in patients with CDKL5 related epilepsy or SCN1A related epilepsy such as Dravet syndrome resulting from a nonsense mutation The secondary objectives of this study are to: Evaluate change in convulsive and/or drop seizure frequency from Baseline following ataluren treatment in patients with CDKL5 related epilepsy or SCN1A related epilepsy such as Dravet syndrome resulting from a nonsense mutation To determine changes in minor seizure types following ataluren treatment in patients with CDKL5 related epilepsy or SCN1A related epilepsy such as Dravet syndrome resulting from a nonsense mutation. (Seizure types as defined by the International League Against Epilepsy [ILAE] criteria. (International League Against Epilepsy. Seizure Classification. 2014. EpilepsyDiagnosis.org)) The exploratory objectives of this study are to: Evaluate change from Baseline in cognitive, motor, and behavioral function as well as quality of life (QOL) following ataluren treatment in patients with CDKL5 related epilepsy or SCN1A related epilepsy such as Dravet syndrome resulting from a nonsense mutation |
| Number of Patients: | 16 evaluable (8 with a CDKL5 nonsense mutation, 8 with a SCN1A nonsense mutation(Dravet syndrome)) |
| Diagnosis and Main Inclusion Criteria: | Age ≥2 years old and ≤12 years old, male or female, at Week 0 (at time informed consent/assent is signed) Documentation of a diagnosis of nonsense mutation in 1 allele for SCN1A deficiency (in particular, Dravet syndrome)or CDKL5 deficiency as evidenced by medical records, genetic testing, and the following clinical feature: Failure to control seizures despite appropriate trial of 2 or more antiepileptic drug (AEDs) at therapeutic doses Current regimen of 1 to 3 baseline AEDs at stable doses for a minimum for 4 weeks prior to enrollment (ie, randomization/Baseline Visit). (Vagus nerve stimulator [VNS], ketogenic diet, and modified Atkins diet do not count towards this limit but must be unchanged for 3 months prior to enrollment.) Minimum of 6 convulsive or drop seizures with duration >3 seconds over the 4 weeks of diary screening prior to randomization |
| Study Product, Dose, Route, Regimen: | Ataluren (oral powder/granules for suspension) Dose: 3 times daily (10 mg, 10 mg and 20 mg/kg morning, midday and evening, respectively) Titration: None Maximum dose: 3 times daily (10 mg, 10 mg, 20 mg/kg morning, midday and evening respectively) |
| Duration of administration: | Each patient receives a total of 12-weeks of active drug (ataluren) and 12-weeks of placebo, in a blinded fashion |

TABLE 2

List Of Abbreviations

| Abbreviation | Definition |
|---|---|
| BUN | blood urea nitrogen |
| CBC | complete blood count |
| CI | confidence interval |
| CMP | comprehensive metabolic panel |

TABLE 2-continued

List Of Abbreviations

| Abbreviation | Definition |
| --- | --- |
| EOS | End of Study |
| IB | Investigator's Brochure |
| ILAE | International League Against Epilepsy |
| ITT | Intent-to-Treat |
| IVRS/IWRS | interactive voice response system/interactive web response system |
| LFT | liver function test |
| LOAEL | lowest-observed-adverse-effect level |
| mRNA | messenger ribonucleic acid |
| PI | Principal investigator |
| PK | pharmacokinetics |
| QOL | Quality of Life |
| QOLCE | Quality of Life in Childhood Epilepsy |
| SAE | Serious adverse event |
| SMEI | severe myoclonic epilepsy of infancy |
| SUDEP | sudden unexpected death in epilepsy |
| TEAE | Treatment-emergent adverse event |
| TID | three (3) times per day |
| VNS | vagus nerve stimulator |

6.2.1. Ataluren

Ataluren (3-[5-(2-fluoro-phenyl)-[1,2,4]oxadiazol-3-yl]benzoic acid) for use in this study is in the form of a white to off-white powder/granules for suspension packaged in child-resistant aluminum foil packets or sachets. Each packet or sachet contains 125, 250 or 1000 mg of drug substance, which is 25% of the total formulation weight.

6.2.1.1. Placebo

The placebo for placebo-controlled clinical studies is provided as a white to off-white powder/granules for suspension. The placebo powder/granules is supplied in packets or sachets matching the fill weights of the active drug product that contain 125, 250, or 1000 mg of the drug substance. The placebo is similar to the active product except that ataluren is replaced by the addition of a filler (microcrystalline cellulose) and an increased amount of mannitol, which together comprise about 50% of the powder/granules.

6.2.2. Study Design

Crossover designs are usually statistically efficient and thus require fewer subjects. Additionally, the influence of confounding covariates is reduced because each crossover patient serves as his or her own control. A 12-week treatment period provides sufficient time to assess changes in the patient's seizure activity and QOL while still allowing appropriate monitoring of the patient. Because treatment options for this patient population are minimal, the dropout rate in this crossover study is expected to be low.

The study is a Phase 2 interventional study which includes the following: Screening (Week −4 to Week 0/Day 1), Treatment Period 1 (Week 0/Day 1-Week 12), Washout Period (Week 12-Week 16), crossover to Treatment Period 2 (Week 16-Week 28), and Follow-up (Week 28-Week 32).

Figure 6:
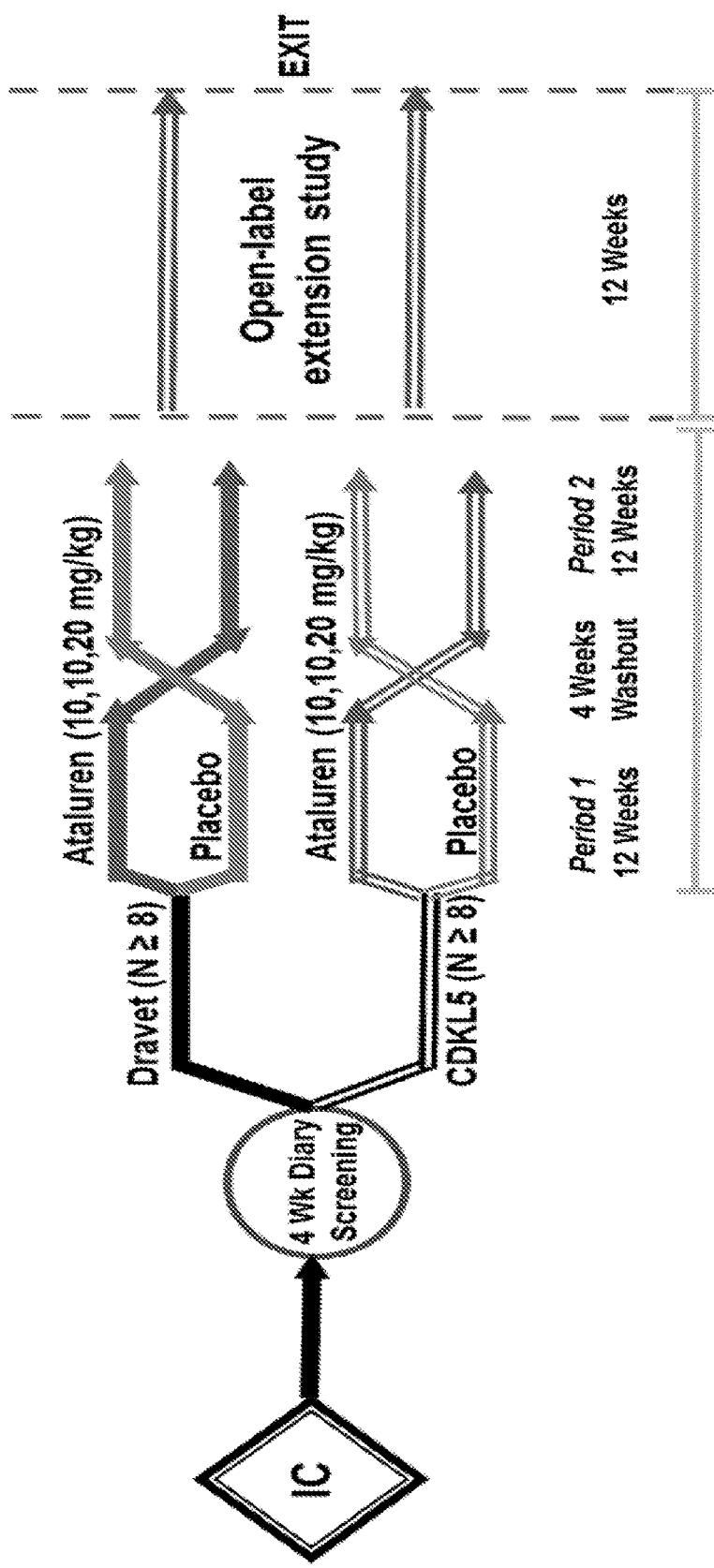
FIG. 6 is a schematic of the study design of the clinical protocol described in Example 6.2 herein.

The study design is shown in FIG. 6. The Schedule of Events is provided in Table 3.

6.2.2.1. Drug Administration Plan

Patients receive 12 weeks of ataluren or placebo during each treatment period. Treatment Period 1 is followed by a 4-week Washout Period. Based on ataluren PK and pharmacodynamic data, the 4-week washout period is deemed an appropriate length of time to eliminate any ataluren drug effects. Following the Washout Period, patients crossover to receive the opposite treatment during Treatment Period 2.

Patients receiving ataluren during Treatment Period 1 receive placebo during Treatment Period 2.

Patients received placebo during Treatment Period 1 receive ataluren during Treatment Period 2.

Study drug is administered 3 times per day (TID). The dose level to be administered is: 10 mg/kg in the morning, 10 mg/kg at midday, and 20 mg/kg in the evening.

Dosing is based on the patient's body weight at baseline. Weight is assessed at every clinic visit. If the patient's body weight changes by ≥10% from baseline, the actual dose may be re-calculated.

The first dose of study drug is administered in the clinic and the date and time of administration is recorded. At the end of each Treatment Period, the last dose of study drug is taken on the evening before the clinic visit (ie, the night before the Visit 6/Week 12 [end of Treatment Period 1] and the night before Visit 18/Week 28 [end of Treatment Period 2]).

6.2.2.2. Research Risks & Benefits

6.2.2.2.1. Risk of Study Drug

All patients are closely monitored for adverse events throughout the study.

Ataluren is a weak inhibitor of CYP2C9 and CYP2C8. Clinical drug interaction studies between ataluren and CYP2C8 and CYP2C9 substrates have not been conducted. Ataluren has the potential to increase the plasma concentration of drugs that are primarily metabolized by CYP2C8 or CYP2C9, which includes drugs with a narrow therapeutic index that are substrates of CYP2C8 or CYP2C9. The effects of other concomitant AEDs and other drug levels metabolized by these enzyme systems are not known, but it may increase their levels leading to potential toxicities. Therefore, AED plasma levels are measured at Baseline and 4 weeks following the first ataluren dose in each Treatment Period (ie, Visit 4/Week 4 and Visit 14/Week 20). AEDs may be adjusted as needed based on signs and symptoms of toxicity and/or changes in drug levels.

6.2.3. Study Objectives

The primary objective of this study is to:
Characterize the safety profile of ataluren in patients with CDKL5 related epilepsy or SCN1A related epilepsy such as Dravet syndrome resulting from a nonsense mutation.

The secondary objectives of this study are to:
Evaluate change in convulsive and/or drop seizure frequency from baseline following ataluren treatment in patients with CDKL5 related epilepsy or SCN1A related epilepsy such as Dravet syndrome resulting from a nonsense mutation.
To determine changes in minor seizure types (absence, myoclonic, complex partial/focal dyscognitive) following ataluren treatment in patients with CDKL5 related epilepsy or SCN1A related epilepsy such as Dravet syndrome resulting from a nonsense mutation.

The exploratory objectives of this study are to:
Evaluate changes from Baseline in cognitive, motor, and behavioral function as well as QOL following ataluren treatment in patients with CDKL5 related epilepsy or SCN1A related epilepsy such as Dravet syndrome resulting from a nonsense mutation.

6.2.4. Endpoints

6.2.4.1. Primary Endpoint

The primary study endpoints of this study include:
Overall safety profile of ataluren characterized by type, frequency, severity, timing, and relationship to study drug of any adverse events or serious adverse events (SAEs); changes in physical examination, laboratory test results, and drug discontinuations due to adverse events or SAE.

6.2.4.2. Secondary Endpoints Primary Endpoint

The secondary endpoints of this study are as follows:

Change in seizure frequency from baseline. Motor seizures to be counted are tonic-clonic seizures, hemiconvulsive seizures, drop attacks, tonic seizures, and focal motor seizures.

The effect on myoclonic seizures (ie, persistence or disappearance) are also be evaluated.

Data is collected during baseline and at each 4 week post-baseline visit to identify changes in:

Number of episodes of status epilepticus, defined as a convulsive lasting >10 minutes Number of uses of rescue medications Number of emergency room visits/hospitalizations 6.2.4.3. Exploratory Endpoints Exploratory endpoints include:

Changes in minor seizure types:

Number of myoclonic seizures

Number of staring (absence or complex partial) seizures

In addition, the severity of epilepsy, cognitive and motor scales, QOL, and safety and tolerability are assessed using the following instruments:
1. Assess clinical and adaptive measures of personality and behavior using the Behavior Assessment System for Children: Third Edition (Sabaz et al. Epilepsy Behav. 2003, 4(6):680-91)
2. Linguistic skills as measured by the Preschool Language Scale, Fourth Edition (PSL-4) (Zimmerman et al 2002)
3. Adaptive level of behavioral function as measured by the Vineland Adaptive Behavior Scales, Second Edition (VABS-II) (Sparrow et al 2005)
4. Quality of Life as assessed by the Quality of Life in Childhood Epilepsy (QOLCE) (Sabaz et al. Epilepsy Behav. 2003, 4(6):680-91)

6.2.4.4. Inclusion Withdrawal

Patients selected for this study must meet the following criteria:
1. Age ≥2 years old ≤12 years old, male or female, at Week 0 (at time informed consent/assent is signed)
2. Documentation of a diagnosis of nonsense mutation in 1 allele for SCN1A deficiency (in particular, Dravet syndrome) or CDKL5 deficiency as evidenced by medical records, genetic testing, and the following clinical feature:
   a. Failure to control seizures despite appropriate trial of 2 or more AEDs at therapeutic doses
3. Between 1 to 3 baseline AEDs at stable doses for a minimum for 4 weeks prior to the Screening visit
   a. Vagus nerve stimulator (VNS), ketogenic diet, and modified Atkins diet do not count towards this limit but must be unchanged for 3 months prior to enrollment.
4. VNS must be on stable settings for a minimum of 3 months prior to the Screening visit
5. If on ketogenic or modified Atkins diet, must be on stable ratio for a minimum of 3 months prior to the Screening visit
6. Written consent obtained from the patient or patient's legal representative must be obtained prior to performing any study procedures
7. Minimum of 6 convulsive or drop seizures with duration >3 seconds over the 4 weeks of diary screening prior to randomization 6.2.4.5. Exclusion Criteria Patients cannot be included in the study if any of the following exclusion criteria are met:
1. Patient is less than 2 years old or more than 12 years old
2. Epilepsies associated with genetic disorders other than SCN1A deficiency (in particular, Dravet syndrome) or CDKL5 deficiency
3. Patient has SCN1A (Dravet) or CDKL5 genetic mutations that are NOT nonsense mutations
4. Felbatol has been initiated within the past 12 months prior to enrollment (Baseline Visit)
5. Patients who are currently or have participated in clinical trials in the past 30 days prior to enrollment (Baseline Visit)
6. Prior or ongoing medical condition (eg, concomitant illness, psychiatric condition), medical history, physical findings, or laboratory abnormality that, in the investigator's opinion, could adversely affect the safety of the patient, makes it unlikely that the course of study drug administration or follow-up would be completed, or could impair the assessment of study results.

6.2.4.6. Patient Recruitment and Screening

Eight nonsense mutation SCN1A (Dravet syndrome) patients and 8 nonsense mutation CDKL5 patients are recruited for the study from the principal investigator (PI) or sub-investigator's clinical practice. During a routine visit, patients/parents/legal guardians that meet criteria for the study are asked if they would like to participate in the study. Male and female patients of any ethnicity between ages of 2 and 12 is assessed for inclusion. During the routine visit, the investigator informs each prospective patient/parent/legal guardian of the nature of the study, explain the potential risks and study-related procedures. If the patient/parent/legal guardian agrees, they are given the informed consent documents to read and sign prior to starting any study procedures. Only the PI, sub-investigators, and other research personnel listed on the study have access to patient information. Once the study patient/parent/legal guardian has signed the informed consent, screening procedures may begin.

6.2.4.7. Randomization

After a patient has completed the necessary screening assessments and has been confirmed to be eligible by the investigator, the patient can be randomized into the study.

Sixteen patients (8 with a CDKL5 nonsense mutation and 8 with a SCN1A nonsense mutation) are enrolled. Within each disorder group, patients are randomized in a 1:1 ratio to 1 of 2 possible treatment assignments during Treatment Period 1:

Placebo

Ataluren (10, 10, 20 mg/kg/day)

6.2.4.8. Blinding

The identity of the treatments is concealed by the use of a placebo that is matched to the active drug in appearance, taste, odor, packaging, labeling, and schedule of administration. Unblinding only occurs in the case of patient emergencies before study completion, if requested by the DMC at the time of the interim DMC review, and at the conclusion of the study. Except for emergency unblinding, individual patients, parents/caregivers, and site personnel are not be informed of the randomized treatment assignments until the implications of revealing such data for the overall ataluren clinical development program have been determined by the investigator.

6.2.5. Early Withdrawal of Patients

6.2.5.1. When and how to Withdraw Patients

A patient may be discontinued from study drug at any time if the patient or patient's legal guardian, or the investigator feels that it is not in the patient's best interest to continue. The following is a list of possible reasons for study drug discontinuation:

1. Parental/guardian withdrawal of consent.
2. Patient is not compliant with study procedures.
3. Protocol violation requiring discontinuation of study drug.
4. Severe adverse events, including significant toxicity such as severe cognitive or behavioral toxicity, impaired liver and renal function, or impaired hematopoiesis.
5. Seizures exacerbation not attributable to other known provocative factors.
6. Interaction with concomitant AED regimen that leads to unacceptable toxicity. Medication adjustments are avoided, if possible, and may require the subject to exit the study, at the discretion of the Investigator.

If patient must discontinue study drug, the method for discontinuation from study drug is determined based on type of reaction and/or reason for withdrawal. For example, if the patient experiences a rapidly progressive rash it would lead to abrupt cessation of study drug, but if patient experiences excess tiredness study drug may be tapered off. A discussion of the method of cessation occurs between the patient and/or patient's parent/legal guardian and the physician.

6.2.5.2. Data Collection and Follow-Up for Withdrawn Patients

For all patients who withdraw from the study, there is one final visit 4 weeks after the last dose of study drug. If the patient/parent/legal guardian cannot be contacted after 4 phone calls to patient/parent/legal guardian, a certified letter is sent to patient/parent/legal guardian.

6.2.6. Study Drug

6.2.6.1. Ataluren

Ataluren is provided as a white to off-white powder/granules for oral suspension. The drug substance and drug product are manufactured under current Good Manufacturing Practices (cGMP) conditions. The formulation includes matrix and suspending agents, surfactants, and various excipients that aid in the manufacturing process. The powder/granules for oral suspension is packaged in aluminum-foil, child-resistant sachets (packets) and supplied in dose strengths containing 125, 250, or 1000 mg of the active drug substance. All of the excipients have been tested to pharmaceutical or food grade and are generally recognized as safe.

6.2.6.2. Placebo

A white to off-white powder/granules placebo formulation is provided for oral suspension. The placebo formulation has been manufactured under cGMP conditions. The dry powder/granules and the liquid suspension of the drug match the active formulation in appearance, odor, and taste. The placebo formulation contains excipients similar to those used in the active product. The placebo is packaged in the same aluminum-foil, child-resistant sachets (packets) matching each of the 125, 250, and 1000 mg dose strengths of active drug sachets.

6.2.6.3. Drug Kits

Drug kits are provided, each of which contains 65 packets or sachets of one of the dose strengths (125, 250, or 1000 mg or matching placebo).

6.2.6.4. Treatment Regimen

Patients receive 12 weeks of blinded ataluren or placebo during each treatment period. Each patient starts at a dose based on their weight in kilograms. The study drug is to be administered in a TID fashion of 10 mg/kg, 10 mg/kg and 20 mg/kg (morning, midday, and evening, respectively). The dose is administered from 125, 250, and 1000 mg foil packets or sachets.

Dosing is based on the patient's body weight at baseline. Weight is assessed at every clinic visit. If the patient's body weight changes by ≥10% from baseline, the actual dose may be re-calculated.

The first dose of study drug is administered in the clinic and the date and time of administration is recorded. At the end of each Treatment Period, the last dose of study drug is taken on the evening before the clinic visit (ie, the night before the Visit 6/Week 12 [end of Treatment Period 1] and the night before Visit 18/Week 28 [end of Treatment Period 2).

Each dose should be taken within ~30 minutes before or after a meal. Intervals for dosing should be ~6 hours (±1 hour) between morning and mid-day doses, ~6 hours (±1 hour) between mid-day and evening doses, and ~12 hours (±1 hour) between evening doses and the morning dose on the next day.

6.2.6.5. Instructions for Delays in Dosing

Dosing delays in study drug (blinded ataluren or placebo) administration should adhere to the following guidelines:
- If dosing of study drug is delayed by ≤1 hour, the planned dose should be taken with no changes to the subsequent dose schedules;
- If study drug dosing is delayed by >1 hour but ≤4 hours, the planned dose should be taken; however, all future doses for that day should be shifted later by an approximately corresponding amount;
- If study drug dosing is delayed by >4 hours, the dose should not be taken. Study drug administration may continue but the missed dose should not be taken and the planned timing of subsequent study drug dosing should not be altered.

6.2.6.6. Study Drug Preparation and Storage

Study drug sachets should be stored at room temperature, away from the reach of children until time of reconstitution and should only be opened at the time of dose preparation. The full contents of each sachet should be mixed with at least 30 mL (1 ounce) of liquid (water, milk, fruit punch), or 3 tablespoons of semi-solid food (yogurt or applesauce). The full contents of the sachets should be mixed with at least 30 mL (1 ounce) of liquid (eg water, milk), or 3 tablespoons of semi-solid food (yogurt, pudding, or applesauce). The prepared dose should be mixed well before administration. The amount of the liquid or semi-solid food can be increased based on patient preference.

Each prepared dose is best administered immediately after preparation. The prepared dose should be discarded if not consumed within 24 hours of preparation if kept refrigerated (2 to 8° C.), or within 3 hours at room temperature (15 to 30° C.). The clinic staff instructs each patient or parent/caregiver on the specific number of sachets to be taken from each kit for each dose and provides detailed oral directions regarding drug preparation. In addition, detailed written drug mixing and dosing instructions are provided to the patient or parent/caregiver when drug supplies are dispensed.

6.2.6.7. Method for Assigning Patients to Treatment Groups

This interventional study contains a placebo portion where patients do not receive active drug therapy beyond the existing background AED regimen. The allocation of ataluren and placebo to treatment number is completed according to a blinded randomization schedule.

Randomization is an accepted means to reduce bias and allows for the highest standard of evidence in documenting a treatment effect. The permuted block randomization technique is used. Such a method allows treatment arms to be balanced with respect to the predefined stratification factors as well as for the number of patients in each arm. The process is established and performed by an experienced clinical research organization (CRO) through an interactive voice response system/interactive web response system (IVRS/IWRS) system to maximize the integrity and security of the randomization and ensure appropriate access and convenience-of-use by the investigational sites. The method should be sufficient to preclude site personnel from making inferences regarding treatment assignments based on known block sizes. A 1:1 randomization of ataluren:placebo is planned in order to avoid the loss of statistical power associated with an unbalanced randomization.

To minimize the potential compromise of study drug blinding and to reduce the chance of inadvertent dosing errors or intentional attempts to mix active drug and placebo within families, if the case occurs, the randomization system allocates subsequently enrolled family members (eg, siblings) to the same treatment group as the first family member enrolled. There is past precedence for this approach [Ballard 2006].

When a patient is randomized in the study and is ready to begin study drug, the PI or qualified designee dispenses the appropriate quantity of blinded study medication and distributes it to the patient and/or patient's parent/legal guardian. Extensive instructions of the correct dosage administration and schedule are discussed and fully understood prior to leaving the appointment.

6.2.6.8. Patient Compliance Monitoring

The study team assesses and tracks patient compliance with the study drug regimen via clinical evaluations and follow-up email or phone calls. The patients are seen for clinical evaluations every month for up to the next 10 months on study drug regimen, with a visit during the first two weeks after first dose of study medication. Any patient who is significantly non-compliant with the study drug regimen (<80% or >120%) is withdrawn from the study as per the PI.

6.2.6.9. Prior and Concomitant Therapy

Throughout the study, including during the Treatment Periods with study drug administration, patients continue their current AED regimen consisting of 1 to 3 drugs at stable doses for at least 4 weeks prior to the Baseline Visit. Concomitant AED concentrations are collected at the Baseline Visit and during the study to assess for the potential interactions. If the patient has a VNS, the settings must be on stable ratio for a minimum of 4 weeks prior to the Baseline Visit. In addition, if the patient is on the ketogenic diet, a stable ratio must have been present for at least 3 months prior to the Baseline Visit. All concomitant AEDs are permitted during the study; felbatol is allowed if dosing has been on a stable dose for ≥12 months prior to enrollment (Baseline). Medication adjustments are avoided, if possible, and may require the subject to exit the study at the discretion of the Investigator.

6.2.6.10. Storage

Sachets containing study drug are stored at controlled room temperature (~15 to 30° C.) in a locked room accessible only to study personnel. The available stability data from representative samples support the use of the drug product for 48 months when stored at room temperature. The stability of the clinical study samples or representative samples may be monitored, as appropriate, to support the clinical study.

6.2.6.11. Dispensing of Study Drug

Dosing of ataluren is based on mg/kg of patient body weight and is adjusted to allow for dosing with up to 3 of the available sachet dose strengths (125 mg, 250 mg, and/or 1000 mg). The entire contents of the sachet is constituted with the constitution medium and is administered. Supply of study drug is calculated based on patient weight and is provided by the PI or qualified designee. Quantity of study drug sachets distributed to each study patient is noted in a study log upon dispensation. Regular study drug reconciliation is performed to document drug assigned and drug remaining. This reconciliation is logged on the drug reconciliation form, and signed and dated by the study team.

6.2.6.12. Overdose Precautions

For any patient experiencing an overdose (administration of an ataluren dose >4 times the intended total daily dose level for this protocol [i.e., >160 mg/kg/day]), observation for any symptomatic side effects should be instituted, and vital signs and biochemical and hematological parameters should be followed closely (consistent with the protocol or more frequently, as needed). Appropriate supportive management to mitigate adverse effects should be initiated. Pending the acquisition of sufficient human experience with the drug, use of gastric lavage or induction of emesis is not specifically recommended nor contraindicated.

6.2.7. Schedule of Events

The types and timing of data to be recorded are summarized in Table 3.

TABLE 3

Schedule of Events

| | Screening[a] | Treatment Period 1[b] | | | | 4-week Washout/ Crossover | Treatment Period 2[b,c] | | | EOS Visit[d] | Follow-up[e] |
|---|---|---|---|---|---|---|---|---|---|---|---|
| Week (±7 days) | −4 (Week −4 to Week 0; Day 28 to Day −1) | 0 | 2 | 4 | 8 | 12 | 16 | 18 | 20 | 24 | 28 | 32 |
| Visit | 1 | 2[f] | 3 | 4 | 6 | 8 | | 10 | 12 | 14 | 16 | 18 | 20 |
| Informed consent/assent | X | | | | | | | | | | | |
| Medical history | X | | | | | | | | | | | |
| Serum viral screen | X | | | | | | | | | | | |

TABLE 3-continued

Schedule of Events

| | Screening[a] | Treatment Period 1[b] | | | | | 4-week Washout/ Crossover | Treatment Period 2[b,c] | | | | EOS Visit[d] | Follow-up[e] |
|---|---|---|---|---|---|---|---|---|---|---|---|---|---|
| Physical examination | X | X | | | | | X | X | | | | X | X |
| Height and weight | X | X | X | X | X | X | X | X | X | X | X | X | X |
| Vital signs | X | X | X | X | X | X | X | X | X | X | X | X | X |
| Seizure data diary provided | X | X | X | X | X | X | | X | X | X | X | X | |
| Seizure data diary collected | | X | X | X | X | X | | X | X | X | X | X | |
| Study drug dispensed | | X[g] | X | X | X | | | X[g] | X | X | X | | |
| Study drug administration | | | X[h] | | | | | | X[h] | | | | |
| Study drug compliance and return | | | X | X | X | X | | | X | X | X | X | |
| Adverse events | X | X | X | X | X | X | | X | X | X | X | X | X |
| Concomitant medications | X | X | X | X | X | X | | X | X | X | X | X | X |
| Blood for CBC, CMP, LFTs, BUN, creatinine levels, serum HCG[i] | X | X | | | | | | X | | | | X | X |
| Blood for plasma PK for AED assessment[j] | | X | X | | | | | X | X | | | | |
| Urinalysis | X | X | | | X | | | X | | | | X | X |
| Behavior Assessment System for Children | | X | | | X | | | X | | | | X | X |
| Preschool Language Scale | | X | | | X | | | X | | | | X | X |
| Vineland Adaptive Behavior Scales | | X | | | X | | | X | | | | X | X |
| Quality of Life in Childhood Epilepsy | | X | | | X | | | X | | | | X | X |

Abbreviations:
AED = antiepilepsy drug;
BUN = blood urea nitrogen;
CBC = complete blood count;
CMP = comprehensive metabolic panel;
EOS = end of study;
HCG = human chorionic gonadotropin;
LFTs = liver function tests;
PK = pharmacokinetics

[a]Screening occurs from Week −4 to Week 0 (i.e., 28 days). The ±7 day visit window is not applicable to the Screening Period.
[b]Odd-numbered visits not shown are conducted by telephone and/or email evaluation
[c]During Treatment Period 2, patients crossover and begin receiving blinded study drug opposite of what they received during Treatment Period 1 (i.e., patients previously receiving blinded ataluren now receive placebo and patients previously receiving placebo now receive ataluren.
[d]The EOS visit is completed for all patients who complete the study and for any patient who discontinues early from the study.
[e]The Follow-up visit is to occur 4 weeks after the EOS visit or last dose of study drug.
[f]Visit 2 is considered the Baseline Visit. Visit 2 must occur no sooner than 28 days and up 42 days after Visit 1. All study and laboratory assessments must be completed prior to the first dose of study drug administration.
[g]The first dose of study drug at Visit 2 (Baseline) and Visit 10 (Week 16) should be given in the clinic.
[h]The last dose of study drug prior to Visit 8/Week 12 (Treatment Period 1) and Visit 18/Week 28 (EOS Visit) should be taken the night before, at home. No morning dose should be taken prior to the clinic visit.
[i]Serum HCG samples taken only for female patients of childbearing potential
[j]Sample to be obtained immediately prior to the morning dose of study drug (trough level only).

6.2.7.1. Screening, Treatment, and Follow-Up Periods

Screening evaluations for the study are performed at the clinical research facility. Study participants report to the clinic on the morning of each scheduled on-site visit and remain in the clinic until released by the investigator after all the study-related procedures have been completed and the patient has been instructed regarding drug storage, reconstitution, and administration.

Adverse events are assessed beginning at the time of informed consent through the end of the follow-up period. Patients must return to the clinic for a follow-up assessment at 4 weeks after the last dose.

6.2.7.1.1. Visit 1 (Screening, 4 Weeks Prior to Baseline Visit 2)

The Screening Visit (Visit 1) occurs 4 weeks prior to Baseline Visit 2 during a routine visit. Screening procedures proceed as follows:

Obtain written informed consent/assent.

Determine if the patient meets the preliminary eligibility criteria:

Collect demographic information
Collect current and relevant medical history
Identify concomitant medications used
Identify and confirm stable use AED medications
If the patient meets the preliminary eligibility criteria, the following assessments are performed:
  Vital signs (including systolic and diastolic blood pressure, radial pulse rate, and body temperature): perform in sitting position
  Physical examination
  Height and weight
  Blood draw for clinical laboratory evaluations:
    blood urea nitrogen (BUN), complete blood count (CBC), comprehensive metabolic panel (CMP), liver function tests (LFTs)
    Serum HCG, as applicable (sample taken only for female patients of childbearing potential)
    Serum viral screen
  Urinalysis
  Instruct patient or patient's parent/legal guardian to keep a seizure diary for the next 4 weeks, including the following information:
    Seizure type, duration, intensity
    Presence or absence of cyanosis
    Use of rescue medications 6.2.7.1.2. Visit 2 (Baseline, Week 0)

After the 4-week Screening period, the diary card provided at the Screening Visit is reviewed and all Inclusion/Exclusion criteria are confirmed. Eligible patients complete the Baseline Visit (Visit 2/Week 0) as follows:
  Physical examination
  Height and weight
  Vital signs (including systolic and diastolic blood pressure, radial pulse rate, and body temperature): performed after the patient has been in a sitting position for 3-5 minutes
  Collect seizure diary and review entries
  Record any adverse events occurring since last visit and any that occur during this visit
  Record any changes in concomitant medications
  Complete the following QOL assessments:
    Behavior Assessment System for Children
    Preschool Language Scale
    Vineland Adaptive Behavior Scales
    QOLCE
  Blood draw for clinical laboratory evaluations
    CBC, CMP, LFTs, BUN, creatinine, serum HCG
    Plasma PK for AED level assessment
  Urinalysis
  Dispense new seizure diary and review instructions for completion
  Dispense blinded study drug and review administration instructions
    TID dosing 10 mg/kg, 10 mg/kg, 20 mg/kg (morning, midday, evening)
    The first dose of study drug should be administered in the clinic after completion of all other assessments and procedures required at this visit.

6.2.7.1.3. Visit 3 (Week 2)

The patient returns to the site for Visit 3. Procedures at Visit 3 proceed as follows:
  Height and weight
  Vital signs (including systolic and diastolic blood pressure, radial pulse rate, and body temperature): performed after the patient has been in a sitting position for 3-5 minutes
  Collect seizure diary and review entries
  Record any adverse events occurring since last visit and any that occur during this visit
  Record any changes in concomitant medications
  Dispense new seizure diary and review instructions for completion
  Dispense blinded study drug and review administration instructions
    TID dosing 10 mg/kg, 10 mg/kg, 20 mg/kg (morning, midday, evening)

6.2.7.1.4. Visit 4 (Week 4)

The patient returns to the site for Visit 4. Procedures at Visit 4 proceed as follows:
  Height and weight
  Vital signs (including systolic and diastolic blood pressure, radial pulse rate, and body temperature): performed after the patient has been in a sitting position for 3-5 minutes
  Collect seizure diary and review entries
  Record any adverse events occurring since last visit and any that occur during this visit
  Record any changes in concomitant medications
  Blood draw plasma PK for AED level assessment
  Dispense new seizure diary and review instructions for completion
  Dispense blinded study drug and review administration instructions
    TID dosing 10 mg/kg, 10 mg/kg, 20 mg/kg (morning, midday, evening)

6.2.7.1.5. Visit 6 (Week 8)

The patient returns to the site for Visit 6. Procedures at Visit 6 proceed as follows:
  Height and weight
  Vital signs (including systolic and diastolic blood pressure, radial pulse rate, and body temperature): performed after the patient has been in a sitting position for 3-5 minutes
  Collect seizure diary and review entries
  Record any adverse events occurring since last visit and any that occur during this visit
  Record any changes in concomitant medications
  Dispense new seizure diary and review instructions for completion
  Dispense blinded study drug and review administration instructions
    TID dosing 10 mg/kg, 10 mg/kg, 20 mg/kg (morning, midday, evening)
  Remind patient/parent/legal guardian that prior to the next clinic visit (Visit 8), the patient should take their final dose of study drug the night before the visit.

6.2.7.1.6. Visit 8 (Week 12 [Beginning of 4 Week Washout])

The patient returns to the site for Visit 8. Visit 8 proceeds as follows:
  Physical examination
  Height and weight
  Vital signs (including systolic and diastolic blood pressure, radial pulse rate, and body temperature): performed after the patient has been in a sitting position for 3-5 minutes
  Collect seizure diary and review entries
  Record any adverse events occurring since last visit and any that occur during this visit
  Record any changes in concomitant medications
  Complete the following QOL assessments:
    Behavior Assessment System for Children
    Preschool Language Scale
    Vineland Adaptive Behavior Scales

QOLCE

Dispense new seizure diary and review instructions for completion

No study drug is dispensed at this visit.

6.2.7.1.7. Treatment Period 2—Visit 10 (Week 16 [Crossover Visit])

The patient returns to the site for Visit 10. Patients crossover and begin receiving blinded study drug opposite of what they received during Treatment Period 1 (i.e., patients previously receiving blinded ataluren now receive placebo and patients previously receiving placebo now receive ataluren). Visit 10 proceeds as follows:

Physical examination

Height and weight

Vital signs (including systolic and diastolic blood pressure, radial pulse rate, and body temperature): performed after the patient has been in a sitting position for 3-5 minutes Collect seizure diary and review entries Record any adverse events occurring since last visit and any that occur during this visit Record any changes in concomitant medications Blood draw for clinical laboratory evaluations CBC, CMP, LFTs, BUN, creatinine, serum HCG Urinalysis Dispense new seizure diary and review instructions for completion Dispense blinded study drug and review administration instructions TID dosing 10 mg/kg, 10 mg/kg, 20 mg/kg (morning, midday, evening)

The first dose of study drug should be administered in the clinic after completion of all other assessments and procedures required at this visit.

6.2.7.1.8. Visit 12 (Week 18)

The patient returns to the site for Visit 12. Visit 12 proceeds as follows:

Height and weight

Vital signs (including systolic and diastolic blood pressure, radial pulse rate, and body temperature): performed after the patient has been in a sitting position for 3-5 minutes Collect seizure diary and review entries Record any adverse events occurring since last visit and any that occur during this visit Record any changes in concomitant medications Dispense new seizure diary and review instructions for completion Dispense blinded study drug and review administration instructions TID dosing 10 mg/kg, 10 mg/kg, 20 mg/kg (morning, midday, evening)

6.2.7.1.9. Visit 14 (Week 20)

The patient returns to the site for Visit 14. Visit 14 proceeds as follows:

Height and weight

Vital signs (including systolic and diastolic blood pressure, radial pulse rate, and body temperature): performed after the patient has been in a sitting position for 3-5 minutes Collect seizure diary and review entries Record any adverse events occurring since last visit and any that occur during this visit Blood draw plasma PK for AED level assessment Record any changes in concomitant medications Dispense new seizure diary and review instructions for completion Dispense blinded study drug and review administration instructions TID dosing 10 mg/kg, 10 mg/kg, 20 mg/kg (morning, midday, evening)

6.2.7.1.10. Visit 16 (Week 24)

The patient returns to the site for Visit 16. Visit 16 proceeds as follows:

Height and weight

Vital signs (including systolic and diastolic blood pressure, radial pulse rate, and body temperature): performed after the patient has been in a sitting position for 3-5 minutes Collect seizure diary and review entries Record any adverse events occurring since last visit and any that occur during this visit Record any changes in concomitant medications Dispense new seizure diary and review instructions for completion Dispense blinded study drug and review administration instructions TID dosing 10 mg/kg, 10 mg/kg, 20 mg/kg (morning, midday, evening)

Remind patient/parent/legal guardian that prior to the next clinic visit (Visit 18), the patient should take their final dose of study drug the night before the visit.

6.2.7.1.11. Visit 18 (Week 28—End of Study Visit [or Early Termination Visit])

The patient returns to the site for Visit 18. This visit is be considered the End of Study (EOS) visit and should be completed for all patients. Patients should have taken their final dose of study drug the night before the clinic visit.

Additionally, any patient who discontinues early from the study should complete this visit.

Visit 18 proceeds as follows:

Physical examination

Height and weight

Vital signs (including systolic and diastolic blood pressure, radial pulse rate, and body temperature): performed after the patient has been in a sitting position for 3-5 minutes Collect seizure diary and review entries Record any adverse events occurring since last visit and any that occur during this visit Record any changes in concomitant medications Complete the following QOL assessments:

Behavior Assessment System for Children

Preschool Language Scale

Vineland Adaptive Behavior Scales

QOLCE

Blood draw for clinical laboratory evaluations

CBC, CMP, LFTs, BUN, creatinine, serum HCG

Urinalysis

No study drug is dispensed at this visit.

6.2.7.1.12. Visit 20 (Week 32 [Follow-Up Visit])

The patient returns to the site for Visit 20. This visit should occur 4 weeks after the final dose of study drug and EOS visit. Visit 20 proceeds as follows:

Physical examination

Height and weight

Vital signs (including systolic and diastolic blood pressure, radial pulse rate, and body temperature): performed after the patient has been in a sitting position for 3-5 minutes Record any adverse events occurring since last visit and any that occur during this visit Record any changes in concomitant medications Complete the following QOL assessments:
Behavior Assessment System for Children
Preschool Language Scale
Vineland Adaptive Behavior Scales
QOLCE
Blood draw for clinical laboratory evaluations
CBC, CMP, LFTs, BUN, creatinine, serum HCG
Urinalysis 6.2.7.1.13. Telephone/Email: Visits 5, 7, 9, 11, 13, 15, 17, and 19

Patients are asked about their study drug dosage to check compliance and how they are tolerating it. Adverse events are assessed and any concerns the patient may have are addressed.

During the contact for Visit 7 and Visit 17, the patient/parent/legal guardian should be reminded that the last dose of study drug should be taken the night before the next clinic visit and no study drug should be taken on the morning of the clinic visit (i.e., Visit 8 or Visit 18).

6.2.7.1.14. Serum Viral Screen

Tests conducted at screening include hepatitis B surface antigen, hepatitis C antibody, and human immunodeficiency virus (HIV). The study manual is referenced for collection, processing, and shipping information.

6.2.7.1.15. Physical Examination

The physical examination (including general appearance, head, eyes, ears, nose, mouth, throat, heart, thyroid, chest and lungs, abdomen, extremities, neuromuscular system, skin, and lymph nodes) is conducted at Screening, Visit 2 (Baseline), Visit 8, Visit 10, Week 18 (EOS or Early Termination), and Follow-up.

Physical examinations may also be performed at any time during the study as clinically indicated.

6.2.7.1.16. Vital Signs

Vital signs (including systolic and diastolic blood pressure, radial pulse rate, and body temperature) are monitored at each clinic visit.

6.2.7.1.17. Height and Weight

Height (in cm) is measured at each clinic visit. Weight (in kg) is measured at each clinic visit.

6.2.7.1.18. Adverse Events

Adverse events are assessed and documented at each scheduled clinic visit, beginning at Screening. If the patient does not visit the clinic on the scheduled day, a telephone call to the patient by qualified site personnel is required to assess adverse events. In addition, subjects/caregivers are encouraged to report adverse events of concern at any time in the intervals between visits.

Additional tests and other evaluations required to establish the significance or etiology of an abnormal result or to monitor the course of an adverse event are obtained when clinically indicated. Patients are followed for adverse events for at least 28 days after the last dose of study drug administration, or until any drug-related adverse events and/or ongoing SAEs have resolved or become stable, whichever is later.

6.2.7.1.19. Concomitant Medications

Concomitant medication information is collected and documented at each scheduled clinic visit. Any concomitant drugs (prescribed or over-the-counter) used during the course of the study and the reason for use is recorded. Information regarding the timing, type, and amount is recorded in a CRF.

6.2.8. Statistics 6.2.8.1. Sample Size Determination

This study is not powered for statistical testing since the primary objective is to characterize the safety profile of ataluren in patients with a CDKL5 or a SCN1A (Dravet syndrome) epileptic disease resulting from a nonsense mutation. Sixteen (16) patients (8 with a CDKL5 nonsense mutation and 8 with a SCN1A nonsense mutation [Dravet syndrome]) are included in this study.

6.2.8.2. Randomization

Sixteen patients (8 with a CDKL5 nonsense mutation and 8 with a SCN1A nonsense mutation [Dravet syndrome]) are enrolled. Within each disorder group, patients are randomized in a 1:1 ratio to 1 of 2 possible treatment assignments during Treatment Period 1:
Placebo
Ataluren (10, 10, 20 mg/kg/day)

After the completion of Treatment Period 1 and a 4-week Washout Period, patients crossover and begin receiving blinded study drug opposite of what they received during Treatment Period 1 (i.e., patients previously receiving blinded ataluren now receive placebo and patients previously receiving placebo now receive ataluren).

6.2.8.3. Populations for Analyses

Intent-to-Treat (ITT) population—The ITT population contain all randomized patients.

6.2.8.4. Efficacy Endpoint Definitions 6.2.8.4.1. Seizures

Seizure activity is assessed based on ILAE criteria for the following:

Motor seizure including tonic-clonic seizures, hemiconvulsive seizures, drop attacks, tonic seizures, focal motor seizures.

Staring seizure is an absence seizure or a complex partial seizure.

Myoclonic seizure is the persistence or disappearance seizure.

Episode of status epilepticus: a convulsive state lasting longer than 10 minutes.

Baseline total number of seizures/ER visits/hospitalizations is defined as the total number of seizures/ER visits/hospitalizations at 4 weeks screening period (Week −4 to Week 0 (Day 1)).

6.2.8.4.2. Clinical and Adaptive Measures of Personality and Behavior

Assessment of clinical and adaptive measures of personality and behavior are made using the Behavior Assessment System for Children ($3^{rd}$ Edition). This is a screening system for measuring behavioral and emotional strengths and weaknesses conducted by the PI or Clinical Research Nurse/Coordinator.

6.2.8.4.2.1. Linguistic Skills

Linguistic skills are measured by the Preschool Language Scale, Fourth Edition (PSL-4) (Zimmerman et al 2002). The assessment is used to evaluate basic communication and language skills in young children and is conducted by the PI or Clinical Research Nurse/Coordinator.

6.2.8.4.2.2. Adaptive Level of Behavioral Function

Adaptive level of behavioral function is measured by the Vineland Adaptive Behavior Scales, Second Edition (VABS-II) (Sparrow et al 2005). The assessment is used to evaluate the child's ability to adapt to practical, everyday skills that are required to function and meet environmental demands. The assessment is conducted by the PI or Clinical Research Nurse/Coordinator.

6.2.8.4.2.3. Quality of Life

Quality of Life is assessed by the QOLCE (Sabaz et al. Epilepsy Behav. 2003, 4(6):680-91). This questionnaire is used to evaluate the QOL of these children living with epilepsy and is distributed to the parents to complete.

6.2.8.5. Statistical Analyses

The confidence interval (CI) for the proportion, if presented, is computed using normal approximation, if the number of the events is at least 5. Otherwise, CI using an exact method is provided. For safety summaries, CI is not presented, unless specified otherwise. Summary statistics are analyzed within each disorder group. All analyses are performed using Statistical Analysis System (SAS®), (Version 9.0 or higher).

6.2.8.5.1. Study Conduct

All protocol deviations are listed and summarized.

6.2.8.5.2. Study Population

Frequency distributions or summary statistics of data pertaining to patient disposition, demographics, baseline characteristics, and medical history are tabulated.

6.2.8.5.2.1. Patient Disposition

The disposition of patients, including the number of patients screened, the number of patients randomized, the number of randomized patients who received at least one dose of study drug, and the number of patients who prematurely discontinue study drug are tabulated.

6.2.8.5.2.2. Demographics and Baseline Characteristics

Demographic and baseline characteristics of patients are summarized descriptively by means and standard deviations for continuous variables, and frequency distribution for categorical variables. Summaries are performed based on all randomized patients (ie, ITT population).

6.2.8.5.2.3. Medical History and Prior Medication

Medical history and prior medication information are summarized.

6.2.8.6. Extent of Exposure

The extent of exposure to ataluren treatment is defined as the last dose date minus the first dose date+1 day. The frequency is presented according to the duration ranges (in days): ≤28 (≤4 weeks), 29 to 56 (4 to 8 weeks), 57 to 84 (8 to 12 weeks), and >84 (>12 weeks). The number of patients in each category as well as the mean duration is also be displayed.

6.2.8.6.1. Discontinuation of Study Therapy

The ITT population is used to summarize discontinuation from study drug as well as the reason for the premature termination of study drug. The proportion of patients who discontinue study drug is summarized using point estimates and 95% CI.

6.2.8.6.2. Treatment Compliance

Study drug compliance is assessed by analysis of unused study drug reported. This information is used to describe and summarize compliance by disorder group and treatment arm. Compliance is assessed in terms of the percentage of drug actually taken relative to the amount that should have been taken during the study.

6.2.8.7. Safety Analyses

All safety presentations are based on the ITT Population and are based only on data included in the analysis period of interest. Listings of all adverse events are also be based on all available data at the scheduled analysis time point. SAE and AE summaries are represented for the following periods:
Up to the end of Visit 8 (Week 12)
Up to the end of Visit 18 (Week 28, EOS Visit)
Between the start of Week 13 and the end of Week 28.
Additional frequency tables summarizing the occurrence of AEs and SAEs after the end of the analysis period of interest is also provided. All AEs and SAEs are summarized by treatment group. Marked laboratory abnormalities are also descriptively summarized. No statistical tests are performed for AEs or laboratory marked abnormalities.

6.2.8.7.1. Adverse Events

Summary information (the number and percent of patients by treatment) is tabulated for:
TEAEs, including clinical and laboratory adverse events
Treatment-related adverse events
TEAEs by severity
Treatment-related adverse events by severity
Serious adverse events
Adverse events leading to discontinuation Summaries are presented by treatment groups and categorized by System Organ Class and Preferred Term. The frequencies of adverse events displayed are the crude rates that represent the number of patients experiencing adverse events divided by the total number of patients.

6.2.8.7.2. Adverse Events Laboratory Parameters

Changes in clinical laboratory tests from baseline (last measurement prior to randomization) and laboratory marked abnormalities (laboratory adverse events) using predefined abnormality criteria are descriptively summarized. In the by-patient analysis, a patient having the same abnormality more than once is counted only once based on the worst severity grade observed.

6.2.8.7.3. Other Parameters

Height, weight, vital signs and physical examination data are descriptively summarized. Concomitant medications by Week 12 and Week 28 are summarized.

6.2.8.8. Efficacy Analyses

All efficacy endpoints are summarized within each disorder group (Dravet or CDKL5) and by treatment group.

Summary statistics for the total numbers of the following measurements during every 4 weeks period since Day 1 (Week 0 to Week 4, Week 4 to Week 8, etc., defined as at "Week 4×X", X=1, 2, . . . , 6), along with changes from baseline are tabulated for the following:
Motor seizures
Staring seizures
Myoclonic seizures
Use of rescue medications
ER visits/hospitalizations To assess the change in total number of motor seizures in each Treatment Period (Treatment Period 1 [from Baseline to Week 12] and Treatment Period 2 [From Visit 10 to the EOS Visit]), ANCOVA models, with the total number of motor seizures at Baseline, body weight, and age as covariates, and the treatment group as factors may be used. In the situation of high level of unbalanceness, mixed effect models are considered. Statistical method for analyzing repeated measures data may also be explored for the change in total number of motor seizures from baseline, as appropriate.

Summary statistics at each measurement time point, along with changes from baseline are tabulated for:
Behavior Assessment System for Children
Preschool Language Scale
Vineland Adaptive Behavior Scales
QOLCE 6.2.9. Safety and Adverse Events 6.2.9.1. Definitions 6.2.9.1.1. Unanticipated Problems Involving Risk to Patients or Others Any incident, experience, or outcome that meets all of the following criteria:
Unexpected in nature, severity, or frequency (ie, not described in study-related documents such as the Institutional Review Board (IRB)-approved protocol or consent form, the IB, etc)
Related or possibly related to participation in the research (ie, possibly related means there is a reasonable possibility that the incident experience, or outcome may have been caused by the procedures involved in the research)

Suggests that the research places patients or others at greater risk of harm (including physical, psychological, economic, or social harm).

6.2.9.1.2. Adverse Event

An adverse event is any symptom, sign, illness or experience that develops or worsens in severity during the course of the study. Intercurrent illnesses or injuries should be regarded as adverse events. Abnormal results of diagnostic procedures are considered to be adverse events if the abnormality:

results in study withdrawal
is associated with a serious adverse event
is associated with clinical signs or symptoms
leads to additional treatment or to further diagnostic tests
is considered by the investigator to be of clinical significance For this protocol, untoward medical occurrences that should be reported as adverse events include the following:

All adverse events that are suspected or are not suspected to be due to study drug.
Overdose (administration of a study drug dose >4 times the highest intended total daily dose level for this protocol [>160 mg/kg/day]) of study drug.
All reactions from medication misuse, abuse, withdrawal, sensitivity, or toxicity.
All reactions that result from medication errors or uses of the study drug outside what is described in the protocol.
Apparently unrelated illnesses, including the worsening of a preexisting illness.
Injury or accidents. Note that if a medical condition is known to have caused the injury or accident (a fall secondary to dizziness), the medical condition (dizziness) and the accident (fall) should be reported as 2 separate adverse events. The outcome of the accident (hip fracture secondary to the fall) should be recorded in source documents.
Abnormalities in physiological testing or physical examination findings that require clinical intervention or further investigation (beyond ordering a repeat [confirmatory] test).
A pre-existing condition (eg, allergic rhinitis) must be noted on the appropriate CRF for Visit 1, but should not be reported as an adverse event unless the condition worsens or episodes increase in frequency during the adverse event reporting period. Diagnostic and therapeutic non-invasive and invasive procedures, such as surgery, should not be reported as adverse events. However, the medical condition for which the procedure was performed should be reported if it meets the definition of an adverse event. For example, an acute appendicitis that begins during the adverse event reporting period should be reported as the adverse event and the resulting appendectomy should be recorded in the source documents. If a surgical procedure was planned prior to entry into the study, and the surgery is not performed because of a worsening of a baseline condition, this should not be reported as an adverse event. Note that, as described in the SAE paragraph below, any inpatient hospitalization occurring as the consequence of an adverse event during the study period should be reported as an SAE.

Each adverse event is to be classified as serious or non-serious by the investigator using medical and scientific judgment.

6.2.9.1.3. Serious Adverse Event

Adverse events are classified as serious or non-serious. A serious adverse event is any AE that is:

fatal
life-threatening
requires or prolongs hospital stay
results in persistent or significant disability or incapacity
a congenital anomaly or birth defect
an important medical event Important medical events are those that may not be immediately life threatening, but are clearly of major clinical significance. They may jeopardize the patient, and may require intervention to prevent one of the other serious outcomes noted above. For example, study drug or other drug overdose or abuse, a seizure that did not result in in-patient hospitalization, or intensive treatment of bronchospasm in an emergency department would typically be considered serious.

Overdose of study drug is considered to be administration of a study drug dose >4 times the intended total daily dose level for this protocol (>160 mg/kg/day). All adverse events that do not meet any of the criteria for serious should be regarded as nonserious adverse events. Note that any SAEs occurring within 4 weeks of the date of last dose should be reported to the investigator.

It will be appreciated that, although specific embodiments of the invention have been described herein for purposes of illustration, the invention described herein is not to be limited in scope by the specific embodiments herein disclosed. These embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description, which modification also intended to be within the scope of this invention.

What is claimed is:

1. A method for treating, ameliorating or managing a nonsense mutation mediated epileptic disease associated with a SCN1A nonsense mutation, comprising administering an effective amount of 3-[5-(2-fluoro-phenyl)-[1,2,4]oxadiazol-3-yl]benzoic acid or a pharmaceutically acceptable salt thereof to a patient having the nonsense mutation mediated epileptic disease.

2. The method of claim 1, wherein the salt is selected from the group consisting of a magnesium salt, a potassium salt, a sodium salt, a tromethamine salt, an L-lysine salt, an L-arginine salt, an N-methyl glucamine salt and an L-histidine salt.

3. The method of claim 1, wherein the epileptic disease is associated with a SCN1A nonsense mutation selected from the group consisting of W192X, R222X, R568X, R701X, R854X, K1017X, W1261X, R1213X, W1408X, W952X, W1284X, S219fsX275, K100fsX1107, L1670fsX1107, and S1846fsX1856.

4. The method of claim 1, wherein the epileptic disease is drug-resistant epilepsy.

5. The method of claim 1, wherein the nonsense mutation mediated epileptic disease is Dravet syndrome.

6. The method of claim 2, wherein the nonsense mutation mediated epileptic disease is Dravet syndrome.

7. The method of claim 3, wherein the epileptic disease is Dravet syndrome.

8. The method of claim 4, wherein the epileptic disease is Dravet syndrome.

* * * * *